United States Patent
Braje et al.

(10) Patent No.: US 8,207,160 B2
(45) Date of Patent: Jun. 26, 2012

(54) TETRAHYDROBENZAZEPINES AND THEIR USE IN HE MODULATION OF THE DOPAMINE D₃ RECEPTOR

(75) Inventors: Wilfried Braje, Rinteln (DE); Andreas Haupt, Schwetzingen (DE); Wilfried Lubisch, Heidelberg (DE); Roland Grandel, Dossenheim (DE); Karla Drescher, Dossenheim (DE); Herve Geneste, Neuhofen (DE); Liliane Unger, Ludwigshafen (DE); Daryl R. Sauer, Trevor, WI (US)

(73) Assignee: Abbott GmbH & Co. KG, Wiesbaden (DE)

( * ) Notice: Subject to any disclaimer, the term of this patent is extended or adjusted under 35 U.S.C. 154(b) by 1070 days.

(21) Appl. No.: 10/583,590

(22) PCT Filed: Dec. 17, 2004

(86) PCT No.: PCT/EP2004/014428
§ 371 (c)(1),
(2), (4) Date: Dec. 12, 2008

(87) PCT Pub. No.: WO2005/058328
PCT Pub. Date: Jun. 30, 2005

(65) Prior Publication Data
US 2009/0105224 A1    Apr. 23, 2009

Related U.S. Application Data

(60) Provisional application No. 60/530,806, filed on Dec. 18, 2003.

(51) Int. Cl.
*A61P 25/00* (2006.01)
*A61K 31/55* (2006.01)
*C07D 223/16* (2006.01)
*C07D 409/12* (2006.01)

(52) U.S. Cl. .................. 514/217.01; 540/594

(58) Field of Classification Search .............. 514/217.01; 540/594
See application file for complete search history.

(56) References Cited

U.S. PATENT DOCUMENTS

| | | | |
|---|---|---|---|
| 2005/0085461 A1* | 4/2005 | Cooper et al. | 514/217.01 |
| 2005/0090485 A1* | 4/2005 | Bromidge et al. | 514/217.01 |
| 2005/0222124 A1* | 10/2005 | Bromidge et al. | 514/217.02 |

FOREIGN PATENT DOCUMENTS

| | | |
|---|---|---|
| DE | 10 131 543 | 1/2003 |
| WO | WO 96/02246 | 2/1996 |
| WO | WO 96/02249 | 2/1996 |
| WO | WO 96/02519 | 2/1996 |
| WO | WO 96/02520 | 2/1996 |
| WO | WO 99/02503 | 1/1999 |
| WO | WO 00/21951 | 4/2000 |
| WO | WO 02/40471 A | 5/2002 |
| WO | WO 03/068732 A | 8/2003 |
| WO | WO 03/068751 A | 8/2003 |
| WO | WO 03/068752 A | 8/2003 |
| WO | WO 03/095428 A | 11/2003 |
| WO | WO 2004/031181 A | 4/2004 |

OTHER PUBLICATIONS

Schwartz J C et al *The Dopamine D3 Receptor as a Target for Antipsychotics* Novel Antipsychotic Drugs, H.Y. Meltzer, ed., Raven Press, New York (1992) pp. 135-144.
Dooley M et al *Pramipexole a Review of its Use in the Management of Early and Advanced Parkinson's Disease* Drugs and Aging vol. 12 (1998) pp. 495-514.
Joyce J N et al *The Dopamine D3 Receptorr as a therapecutic Target for Antipsychotic and Antiparkinsonian Drugs* Pharmacology and Therapeutics vol. 90 (2001) pp. 231-259.
Sokoloff P et al *Localization and Functioin of the D3 Dopamine Receptor* Arzneim. Forsch./Drug Res. vol. 42(1) (1992) pp. 224-230.
Sokoloff P et al *Molecular Cloning and Characterization of a Novel Dopamine Receptor (D3) as a Targe for Neuroleptics* Nature vol. 347 (1990) pp. 146-151.

* cited by examiner

*Primary Examiner* — Brenda Coleman
(74) *Attorney, Agent, or Firm* — Lisa V. Mueller; Michael Best & Friedrich LLP

(57) ABSTRACT

The invention relates to tetrahydrobenzazepines of the general formula I

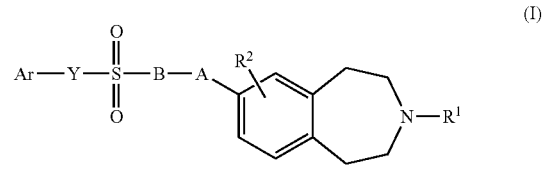

in which the variables Ar, A, B, Y, $R^1$ and $R^2$ have the meanings indicated in claim 1, as well as the N-oxides of these compounds, the physiologically tolerated acid addition salts of these compounds and the physiologically tolerated acid addition salts of the N-oxides.
The invention also relates to a pharmaceutical composition that comprises at least one tetrahydrobenzazepine compound of the formula I, the physically tolerated acid addition salt of I, the N-oxide of compound of the formula I and/or the physically tolerated acid addition salts of the N-oxides of I, and further to the use of a compound according to the present invention for treating disorders that respond beneficially to dopamine $D_3$ receptor antagonists or dopamine $D_3$ agonists. The compounds according to the invention are preferably useful for the treatment of disorders of the central nervous system such as schizophrenia and depression and for the treatment of renal function disorders.

15 Claims, No Drawings

TETRAHYDROBENZAZEPINES AND THEIR USE IN HE MODULATION OF THE DOPAMINE D₃ RECEPTOR

CROSS-REFERENCE TO RELATED APPLICATION

This applications claims priority of international application no. PCT/EP2004/014428 filed Dec. 17, 2004, which claims priority of U.S. patent application Ser. Nos. 10/740,092 filed Dec. 18, 2003 and 60/530,806 filed Dec. 18, 2003.

The present invention relates to novel tetrahydrobenzazepines. The compounds have valuable therapeutic properties and are suitable in particular for the treatment of disorders which respond to modulation of the dopamine $D_3$ receptor.

Neurons receive their information inter alia via G-protein-coupled receptors. There are numerous substances which exert their effect via these receptors. One of them is dopamine. There are confirmed findings concerning the presence of dopamine and its physiological function as neurotransmitter. Disturbances in the dopaminergic transmitter system result in disorders of the central nervous system, examples of which include schizophrenia, depression or Parkinson's disease. These and other disorders are treated with medicaments which interact with dopamine receptors.

Until 1990, two subtypes of dopamine receptors were clearly defined pharmacologically, namely the $D_1$ and $D_2$ receptors. More recently, a third subtype has been found, namely the $D_3$ receptor which appears to mediate some effects of antipsychotics and antiparkinson agents (J. C. Schwartz et al., The Dopamine $D_3$ Receptor as a Target for Antipsychotics, in Novel Antipsychotic Drugs, H. Y. Meltzer, Ed. Raven Press, New York 1992, pages 135-144; M. Dooley et al., Drugs and Aging 1998, 12, 495-514, J. N. Joyce, Pharmacology and Therapeutics 2001, 90, pages 231-59 "The Dopamine $D_3$ Receptor as a Therapeutic Target for Antipsychotic and Antiparkinsonian Drugs").

Dopamine receptors are now divided into two families. On the one hand, the $D_2$ group consisting of $D_2$, $D_3$ and $D_4$ receptors and, on the other hand, the $D_1$ group consisting of $D_1$ and $D_5$ receptors. Whereas $D_1$ and $D_2$ receptors are widespread, $D_3$ receptors by contrast appear to be regioselectively expressed. Thus, these receptors are preferentially found in the limbic system, the projection regions of the mesolimbic dopamine system, especially in the nucleus accumbens, but also in other regions such as the amygdala. Because of this comparatively regioselective expression, $D_3$ receptors are regarded as a target with few side effects, and it is assumed that a selective $D_3$ ligand ought to have the properties of known antipsychotics but not their dopamine $D_2$ receptor-mediated neurological side effects (P. Sokoloff et al., Localization and Function of the $D_3$ Dopamine Receptor, Arzneim. Forsch./Drug Res. 42(1), 224 (1992); P. Sokoloff et al. Molecular Cloning and Characterization of a Novel Dopamine Receptor ($D_3$) as a Target for Neuroleptics, Nature, 347, 146 (1990)).

Compounds with dopamine $D_3$ receptor affinity have been described repeatedly in the prior art, e.g. in WO 96/02519, WO 96/02520, WO 96/02249, WO 96/02246 and DE 10131543 and WO 99/02503. Some of these compounds have high affinities for the dopamine $D_3$ receptor. They are therefore proposed for the treatment of disorders of the central nervous system.

WO 00/21951 describes tetrahydrobenzazepine compounds of the general formula I

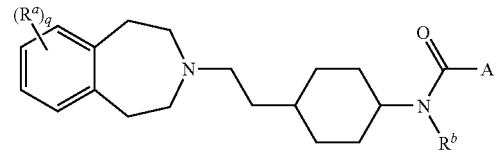

in which A is an aromatic or heteroaromatic radical or a group which carries an aromatic or heteroaromatic radical, $R^a$ is inter alia hydrogen, halogen, CN, acetyl, 3-methyloxa-1,4-diazol-1-yl, pyridyl, pyrimidinyl, 5-methylisoxazol-3-yl, pyrrolidinylcarbonyl or methylsulfonyloxy, q is 1 or 2, and $R^b$ is hydrogen or an alkyl group. Compounds of this type display moderate selectivities for the dopamine D3 receptor in relation to the dopamine D2 receptor.

WO 02/40471 describes tetrahydrobenzazepine compounds of the general formula I

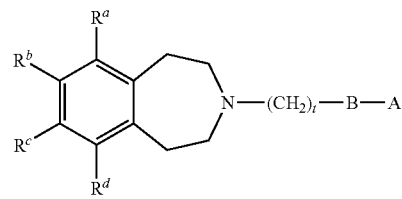

in which A is a heteroaromatic radical, B is sulfur or a $CH_2$ group, t is 3 or 4, $R^a$ and $R^d$ are independently of one another H, F, Cl, Br, OH, CN, alkyl, alkoxy, or $NO_2$, and $R^b$ and $R^c$ are independently of one another hydrogen or a large number of possible substituents. $R^b$ is preferably a substituent different from hydrogen, in particular alkylsulfonyl, alkylsulfonyloxy, (di)alkylaminosulfonyl, N-heterocyclylsulfonyl, e.g. N-pyrrolidinylsulfonyl, N-morpholinylsulfonyl, N-piperidinylsulfonyl, or a heteroaromatic group such as 5-methylisoxazol-3-yl, or 3-methyloxazolyl. Compounds of this type display moderate selectivities for the dopamine D3 receptor in relation to the dopamine D2 receptor.

The object on which the invention is based is to provide compounds which act as selective dopamine $D_3$ receptor ligands.

This object is achieved by the tetrahydrobenzazepines of the general formula I

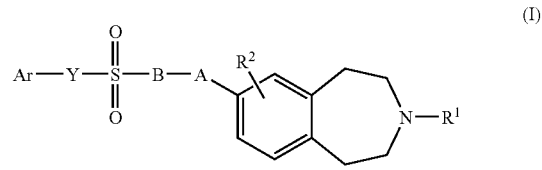

in which
A is a single bond or $CH_2$;
B is a single bond or a group $NR^3$;
Y is a single bond, $CH_2$ or a group $NR^3$, where A, B and Y are not simultaneously a single bond;
Ar is an aromatic radical which is selected from phenyl and a 5- or 6-membered heteroaromatic radical having 1, 2, 3 or 4 heteroatoms which are selected independently of one another from O, N and S, where the aromatic radical may have 1, 2 or 3 substituents which are selected independently of one another from $C_1$-$C_6$-alkyl which is optionally substituted one or more times by OH, $C_1$-$C_4$-alkoxy, halogen or phenyl, or $C_2$-$C_6$-alkenyl which is optionally substituted one or more times by OH, $C_1$-$C_4$-alkoxy, halogen or phenyl, or $C_2$-$C_6$-alkynyl which is optionally substituted one or more times, e.g. 1, 2 or 3 times, by OH, $C_1$-$C_4$-alkoxy, halogen or phenyl, or $C_3$-$C_6$-cycloalkyl which is optionally substituted one or more times by OH, $C_1$-$C_4$-alkoxy, halogen, phenyl or $C_1$-$C_4$-alkyl, or halogen, CN, $OR^4$, $COOR^4$, $NR^5R^6$, $CONR^5R^6$, $NO_2$, $SR^7$, $SO_2R^7$, $SO_2NR^5R^6$, $COR^8$, and phenyl which optionally has one, two or three substituents which are selected independently of one another from $C_1$-$C_4$-alkyl, $C_1$-$C_4$-alkoxy, $NR^5R^6$, CN, $C_1$-$C_2$-fluoroalkyl or halogen, where phenyl and the heterocyclic radical may also be fused to a 5- or 6-membered aromatic or nonaromatic carbocycle, or phenyl may be fused to a 5- or 6-membered aromatic or nonaromatic heterocycle which has 1, 2 or 3 heteroatoms selected from O, N and S;

$R^1$ is hydrogen, $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_1$-$C_8$-alkylcarbonyl, $C_1$-$C_8$-haloalkylcarbonyl or substituted $C_1$-$C_8$-alkyl which carries a substituent which is selected from OH, $C_1$-$C_4$-alkoxy, $C_1$-$C_4$-alkylamino, Di-($C_1$-$C_4$-alkyl)amino, phenyl, phenoxy, $C_3$-$C_8$-cycloalkyl and $C_3$-$C_8$-cycloalkyloxy, where the last four groups mentioned may optionally have one or more, e.g. 1, 2 or 3, substituents selected from OH, CN, $NO_2$, $C_1$-$C_4$-alkyl, $C_1$-$C_4$-haloalkyl, $C_1$-$C_4$-alkoxy, $C_1$-$C_4$-haloalkoxy and halogen;

$R^2$ is hydrogen, halogen, $C_1$-$C_4$-alkyl, $C_1$-$C_4$-haloalkyl, $C_1$-$C_4$-haloalkoxy, $C_1$-$C_4$-alkoxy, OH, $NO_2$, CN, $COOR^4$, $NR^5R^6$ or $CONR^5R^6$;

$R^3$ is hydrogen, $C_1$-$C_4$-alkyl, $C_1$-$C_4$-alkoxy, $C_1$-$C_4$-alkylcarbonyl, phenyl, phenyl-$C_1$-$C_4$-alkyl or phenylcarbonyl, where phenyl in the last three radicals mentioned may optionally have 1, 2 or 3 substituents which are selected independently of one another from $C_1$-$C_4$-alkyl, $C_1$-$C_4$-haloalkyl, $C_1$-$C_4$-alkoxy and halogen;

$R^4$ to $R^8$ are independently of one another H, $C_1$-$C_6$-alkyl which optionally carries a substituent, selected from OH, $C_1$-$C_4$-alkoxy and optionally substituted phenyl, $C_1$-$C_6$-haloalkyl or phenyl, where $R^6$ may also be a group $COR^9$ in which $R^9$ is H, $C_1$-$C_6$-alkyl which is optionally substituted by OH, $C_1$-$C_4$-alkoxy or optionally substituted phenyl, or $C_1$-$C_6$-haloalkyl or phenyl, where $R^5$ with $R^6$ may also together with the nitrogen atom to which they are bonded be a 5- or 6-membered saturated or unsaturated N-heterocycle which may optionally have a further heteroatom selected from O, S and $NR^{10}$ as ring member, where $R^{10}$ is hydrogen or $C_1$-$C_4$-alkyl;

the N-oxides of these compounds, the physiologically tolerated acid addition salts of these compounds and the physiologically tolerated acid addition salts of the N-oxides.

The present invention therefore relates to tetrahydrobenzazepines of the general formula I, to their N-oxides and to their physiologically tolerated acid addition salts and to the physiologically tolerated acid addition salts of the N-oxides.

The present invention also relates to the use of tetrahydrobenzazepines of the general formula I, of their N-oxides and of their acid addition salts for producing a pharmaceutical composition for the treatment of disorders which respond to the influence of dopamine $D_3$ receptor antagonists or agonists.

The disorders which respond to the influence of dopamine $D_3$ receptor antagonists or agonists include in particular disturbances and disorders of the central nervous system, especially affective disorders, neurotic disorders, stress disorders and somatoform disorders and psychoses, specifically schizophrenia and depression, and in addition renal function disorders, especially renal function disorders caused by diabetes mellitus (see WO 00/67847).

The aforementioned indications are treated according to the invention by using at least one compound of the general formula I having the meanings mentioned at the outset. Where the compounds of the formula I have one or more centers of asymmetry, it is also possible to employ mixtures of enantiomers, especially racemates, mixtures of diastereomers, mixtures of tautomers, preferably the respective substantially pure enantiomers, diastereomers and tautomers.

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids such as methanesulfonic acid, aromatic sulfonic acids such as benzenesulfonic acid and toluenesulfonic acid, oxalic acid, maleic acid, fumaric acid, lactic acid, tartaric acid, adipic acid or benzoic acid. Further acids which can be used are described in Fortschritte der Arzneimittelforschung, volume 10, pages 224 et seq., Birkhäuser Verlag, Basel and Stuttgart, 1966.

It is likewise possible to use N-oxides of the compounds of the formula I or their salts with physiologically tolerated acids. In the N-oxides of the compounds of the formula I, one or more of the N atoms which are ring members, and especially ring members in the aromatic heterocycles Q and/or Ar, are in the form of the N-oxide group. Preferred N-oxides of I are those in which the nitrogen of the tetrahydroazepine moiety carries an oxygen atom.

Halogen here and hereafter is fluorine, chlorine, bromine or iodine.

$C_n$-$C_m$-Alkyl (also in radicals such as alkoxy, alkylthio, alkylamino, dialkylamino, alkylcarbonyl etc.) is a straight-chain or branched alkyl group having n to m carbon atoms, e.g. 1 to 8, preferably 1 to 6, and in particular 1 to 4, carbon atoms. Examples of an alkyl group are methyl, ethyl, n-propyl, isopropyl, n-butyl, 2-butyl, isobutyl, tert-butyl, n-pentyl, 2-pentyl, neopentyl, n-hexyl and the like.

$C_1$-$C_6$-Alkyl may where indicated have one or more, e.g. 1, 2 or 3, substituents which are selected from OH, $C_1$-$C_4$-alkoxy, halogen or phenyl. In the case of OH, $C_1$-$C_4$-alkoxy and phenyl there is in particular only one substituent. Such radicals are also referred to hereinafter as $C_1$-$C_4$-alkoxy-$C_1$-$C_6$-alkyl such as methoxymethyl, 1- or 2-methoxyethyl, 1-methoxy-1-methylethyl or 2-methoxy-1-methylethyl, 1-, 2- or 3-methoxypropyl, ethoxymethyl, 1- or 2-ethoxyethyl, hydroxy-$C_1$-$C_6$-alkyl, 1-hydroxymethyl, 1- or 2-hydroxyethyl, 1-hydroxy-1-methylethyl, 1-, 2- or 3-hydroxypropyl etc., or phenyl-$C_1$-$C_6$-alkyl. In the case of halogen substituents, these radicals are also referred to as haloalkyl.

$C_1$-$C_8$-Haloalkyl (also in radicals such as haloalkoxy) is an alkyl group having 1 to 8, preferably 1 to 6, and in particular 1 to 4, C atoms, as defined above, in which all or some, e.g. 1, 2, 3, 4 or 5, of the hydrogen atoms are replaced by halogen atoms, in particular by chlorine or fluorine. Preferred haloalkyl is $C_1$-$C_2$-fluoroalkyl or $C_1$-$C_2$-fluorochloroalkyl, i.e. $C_1$-$C_2$-alkyl in which 1, 2, 3, 4 or 5 hydrogen atoms are replaced by fluorine or chlorine, in particular $CF_3$, $CHF_2$, $CF_2Cl$, $CH_2F$, $CH_2CF_3$ and $CH_2CH_2F$.

$C_3$-$C_6$-Cycloalkyl is a cycloaliphatic radical having 3 to 6 C atoms such as cyclopropyl, cyclobutyl, cyclopentyl and cyclohexyl.

$C_2$-$C_8$-Alkenyl is a monounsaturated linear or branched hydrocarbon radical having 2, 3, 4, 5, 6, 7 or 8 C atoms, e.g.

vinyl, allyl (2-propen-1-yl), 1-propen-1-yl, 2-propen-2-yl, methallyl (2-methylprop-2-en-1-yl) and the like. $C_3$-$C_4$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl, 2-ethylprop-2-en-1-yl.

$C_2$-$C_6$-Alkenyl may where indicated have one or more, e.g. 1, 2 or 3, substituents which are selected from OH, $C_1$-$C_4$-alkoxy, halogen or phenyl. In the case of OH, $C_1$-$C_4$-alkoxy and phenyl there is in particular only one substituent. Such radicals are also referred to hereinafter as $C_1$-$C_4$-alkoxy-$C_2$-$C_6$-alkenyl such as 1- or 2-methoxyethen-1-yl, 1-, 2- or 3-methoxypropen-1-yl etc., hydroxy-$C_2$-$C_6$-alkenyl such as 3-hydroxypropen-1-yl or -2-yl, or phenyl-$C_2$-$C_6$-alkenyl such as 1- or 2-phenylethen-1-yl. In the case of halogen substituents, these radicals are also referred to as haloalkenyl (see above).

$C_2$-$C_8$-Haloalkenyl is an alkenyl group as defined above, in which all or some, e.g. 1, 2, 3, 4 or 5, of the hydrogen atoms are replaced by halogen atoms, in particular by chlorine or fluorine.

$C_2$-$C_8$-Alkynyl is a hydrocarbon radical having 2, 3, 4, 5, 6, 7 or 8 C atoms and having a triple bond, e.g. propargyl (2-propyn-1-yl), 1-methylprop-2-yn-1-yl, 2-butyn-1-yl, 3-butyn-1-yl, 2-pentyn-1-yl, 1-pentyn-3-yl etc.

$C_2$-$C_6$-Alkynyl may where indicated have one or more, e.g. 1, 2 or 3, substituents which are selected from OH, $C_1$-$C_4$-alkoxy, halogen or phenyl. In the case of OH, $C_1$-$C_4$-alkoxy and phenyl there is in particular only one substituent. Such radicals are also referred to hereinafter as $C_1$-$C_4$-alkoxy-$C_2$-$C_6$-alkynyl such as 2-methoxyethyn-1-yl, 3-methoxypropyn-1-yl etc., hydroxy-$C_2$-$C_6$-alkenyl such as 3-hydroxypropyn-1-yl, or phenyl-$C_2$-$C_6$-alkynyl such as phenylethynyl. In the case of halogen substituents, these radicals are also referred to as haloalkenyl (see above).

$C_2$-$C_8$-Haloalkynyl is an alkenyl group as defined above, in which all or some, e.g. 1, 2, 3, 4 or 5, of the hydrogen atoms are replaced by halogen atoms, in particular by chlorine or fluorine.

Phenyl-$C_1$-$C_4$-alkyl is a $C_1$-$C_4$-alkyl radical as defined above in which one hydrogen atom is replaced by a phenyl radical, as in benzyl or 2-phenylethyl.

Optionally substituted phenyl is phenyl that optionally has one or more, e.g. 1, 2 or 3, of the following substituents: halogen, $C_1$-$C_4$-alkyl, $C_1$-$C_4$-alkoxy, hydroxy, nitro, $NH_2$, cyano, COOH, $C_1$-$C_4$-alkoxycarbonyl, $C_1$-$C_4$-alkylcarbonyl, $C_1$-$C_4$-alkylamino, di-($C_1$-$C_4$-alkyl)amino, $C_1$-$C_4$-alkylsulfonyl, $C_1$-$C_4$-alkylsulfonylamino and/or $C_1$-$C_4$-alkylaminosulfonyl.

Examples of 5-membered heteroaromatic radicals are those having 1, 2, 3 or 4 heteroatoms as ring members, which are selected independently of one another from O, N and S, e.g. pyrrole, thiophene, furan, oxazole, isoxazole, thiazole, isothiazole, imidazole, 1,2,3-thiadiazole, 1,2,4-thiadiazole, 1,3,4-thiadiazole, 1,2,3-triazole, 1,2,4-triazole, 1,3,4-triazole, tetrazole. The 5-membered heteroaromatic radicals may have the substituents indicated above and/or be fused to a nonaromatic or aromatic carbocycle, in particular a benzene or cyclohexene ring, as in indole, benzo[b or c]thiophene, benzo[b or c]furan, benz[b]oxazole, benzo[c or d]isoxazole, benz[b]thiazole, benzo[b]imidazol or benzo[c or d]isothiazole. Examples of 6-membered heteroaromatic radicals having 1 or 2 nitrogen atoms as ring members are, in particular, 2-, 3- or 4-pyridinyl, 2-, 4- or 5-pyrimidinyl, 2- or 3-pyrazinyl and 3- or 4-pyridazinyl. The 6-membered heteroaromatic radicals may have the substituents indicated above and/or be fused to a nonaromatic or aromatic carbocycle, in particular a benzene or cyclohexene ring, as in benzo[b]pyridine (=quinoline), benzo[c]pyridine (isoquinoline), benzo[b]pyrimidine (quinazoline), cinnoline, phthalazine or quinoxaline. In the 5- or 6-membered heteroaromatic radicals, the linkage to the group Y takes place via the heterocycle.

Where Ar is phenyl, the phenyl group may also be fused to an aromatic or heteroaromatic 5- or 6-membered ring of the type mentioned above, e.g. to a 5- or 6-membered aromatic or nonaromatic heterocycle which has 1, 2 or 3 heteroatoms selected from O, N and S, e.g. to pyridine, pyrimidine, pyrazine, pyridazine, furan, thiophene, oxazole, isoxazole, thiazole, isothiazole, 1,4-dioxane, 1,4-oxazinane or 1,3-dioxolane, as in benzo[b]pyridine (=quinoline), benzo[c]pyridine (isoquinoline), indole, benzo[b or c]thiophene, benzo[b or c]furan, benz[b]oxazole, benz[c or d]isoxazole, benz[b]thiazole, benzo[b]imidazole, benzo[c or d]isothiazole, benzo[b]pyrimidine (quinazoline), cinnoline, phthalazine, quinoxaline, chromene, chroman, benzo[b]piperazine, benzo[b or c]piperidine, benzo[b]-1,4-oxazinane, benzo[b]-1,3-dioxolane or benzo[b]-1,4-dioxane. Phenyl may also to a 5- or 6-membered carbocycle, e.g. to benzene, cyclohex(adi)ene, cylopent(adi)ene, as in naphthanline, indane, indene or in di- or tetrahydronaphthalene. In radicals of this type, Ar is linked to the group Y via the phenyl ring.

A first preferred embodiment of the invention relates to (het)arylsulfonamides of tetrahydro benzazepine, i.e. compounds of the formula I, in which A and Y are a single bond, and B is a group $NR^3$. Compounds of this type are also referred to hereinafter as (het)arylsulfonamides I.A or as compounds I.A.

A second preferred embodiment of the invention relates to (het)arylsulfomethyl compounds of tetrahydro benzazepine, i.e. compounds of the formula I in which A is $CH_2$, and B and Y are each a single bond. Compounds of this type are also referred to hereinafter as (het)arylsulfomethyl compounds I.B or as compounds I.B.

A third preferred embodiment of the invention relates to (het)arylaminosulfones of tetrahydro benzazepine, i.e. compounds of the formula I in which A and B together are a single bond, and Y is a group $NR^3$. Compounds of this type are also referred to hereinafter as (het)arylaminosulfones I.C or as compounds I.C.

A fourth preferred embodiment of the invention relates to (het)arylmethylsulfonyl compounds of tetrahydro benzazepine, i.e. compounds of the formula I in which Y is $CH_2$, and A and B together are a single bond. Compounds of this type are also referred to hereinafter as (het)arylmethylsulfonyl compounds I.D or as compounds I.D.

With a view to the use of the compounds of the invention as dopamine $D_3$ receptor ligands, compounds I.A and I.B are particularly preferred.

With a view to the use of the compounds of the invention as dopamine $D_3$ receptor ligands, $R^1$ in formula 1 is a radical of the formula $CH_2$—$R^{1a}$ in which $R^{1a}$ can have the following meanings:

$C_1$-$C_7$-alkyl, $C_1$-$C_7$-haloalkyl, $C_2$-$C_7$-alkenyl, $C_2$-$C_7$-haloalkenyl, $C_2$-$C_7$-alkynyl, $C_2$-$C_7$-haloalkenyl, $C_1$-$C_7$-alkyl which has a substituent which is selected from OH, $C_1$-$C_4$-alkoxy, $C_1$-$C_4$-alkylamino, di-($C_1$-$C_4$-alkyl) amino, phenyl, phenoxy, $C_3$-$C_8$-cycloalkyl and $C_3$-$C_8$-cycloalkyloxy, where the last 4 groups mentioned may optionally have one or more, e.g. 1, 2, 3 or 4, substituents selected from $C_1$-$C_4$-alkyl, $C_1$-$C_4$-haloalkyl, $C_1$-$C_4$-alkoxy and halogen, $C_1$-$C_4$-alkoxy, $C_1$-$C_4$-alkylamino, di-$C_1$-$C_4$-alkylamino, $C_3$-$C_8$-cycloalkyl, $C_3$-$C_8$-cycloalkyloxy, each of which may optionally have one or more, e.g. 1, 2, 3 or 4, substituents selected from $C_1$-$C_4$-alkyl, $C_1$-$C_4$-haloalkyl, $C_1$-$C_4$-haloalkoxy, $C_1$-$C_4$-alkoxy and halogen.

Phenyl or phenoxy, each of which may optionally have one or more, e.g. 1, 2, 3 or 4, substituents selected from $C_1$-$C_4$-alkyl, $C_1$-$C_4$-haloalkyl, $C_1$-$C_4$-alkoxy, $C_1$-$C_4$-haloalkoxy and halogen.

Compounds I preferred among these are those in which $R^{1a}$ is $C_1$-$C_7$-alkyl, $C_2$-$C_7$-alkenyl, $C_2$-$C_7$-alkynyl, $C_3$-$C_8$-cycloalkyl or $C_1$-$C_7$-fluoroalkyl, and specifically methyl, ethyl, fluoromethyl, trifluoromethyl, 2-fluoroethyl, 2,2,2-trifluoroethyl, cyclopropyl or vinyl, with most preference given to ethyl.

In another embodiment of the invention, $R^1$ is trifluoroacetyl. Compounds of this type are of interest in particular as intermediates for preparing other compounds I of the invention, because the trifluoroacetyl group represents an effective protective group for the nitrogen in the tetrahydrobenzazepine ring.

With a view to the use of the compounds of the invention as dopamine $D_3$ receptor ligands, the variables $R^2$ and Ar preferably have independently of one another the following meanings:

$R^2$ is hydrogen, halogen, specifically chlorine or fluorine, $C_1$-$C_4$-alkyl, specifically methyl, $C_1$-$C_4$-haloalkyl, specifically trifluoromethyl or difluoromethyl, nitro, $C_1$-$C_4$-alkoxy, specifically methoxy. $R^2$ is, in particular, hydrogen.

Preferred substituents on Ar are e.g. $C_2$-$C_6$-alkyl, $C_2$-$C_6$-alkenyl, $C_2$-$C_6$-alkynyl and $C_1$-$C_4$-fluoroalkyl, in particular ethyl, isopropyl, tert-butyl, vinyl and trifluoromethyl.

Ar is preferably 2, 3- or 4-pyridyl, 2- or 3-thienyl or, in particular, phenyl, each of which optionally have 1, 2 or 3, in particular at least one, of the aforementioned substituents.

With a view to the use of compounds of the invention as dopamine $D_3$ receptor ligands, preferred compounds of the formula I are those in which Ar has a substituent $R^P$ in the para position and, where appropriate a further substituent, which is different from hydrogen, $R^{o/m}$ in the ortho or in the meta postion, in each case relative to the point of linkage to the Y or $SO_2$ group. The radicals $R^P$ and $R^{o/m}$ may be identical or different. The radicals $R^P$ in the para position are preferably selected from halogen, $C_2$-$C_6$-alkyl, $C_2$-$C_6$-alkenyl, $C_2$-$C_6$-alkynyl, and $C_1$-$C_4$-fluoroalkyl and, in particular, ethyl, vinyl, isopropyl, tert-butyl and trifluoromethyl. Preferred radicals $R^{o/m}$ are selected from halogen, specifically chlorine and fluorine, $C_1$-$C_4$-alkyl, specifically methyl, trifluoromethyl. In a particularly preferred embodiment, Ar has only one substituent in the para position.

A very preferred embodiment relates to compounds of the formula I, in particular to the compounds of the formulae I.A and I.B, wherein Ar is phenyl that carries a radical $R^P$ in the para position of the phenyl ring, wherein $R^P$ has the following formula:

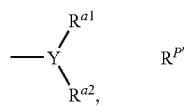

wherein
Y is N, CH or CF,
$R^{a1}$ and $R^{a2}$ are independently of each other selected from $C_1$-$C_2$-alkyl, fluorinated $C_1$-$C_2$-alkyl, provided for Y being CH or CF one of the radicals $R^{a1}$ or $R^{a2}$ may also be hydrogen or fluorine, or $R^{a1}$ and $R^{a2}$ form a radical $(CH_2)_m$ wherein 1 or 2 of the hydrogen atoms may be replaced by fluorine and wherein m is 2, 3 or 4.

In particular, the radical $R^{P'}$ is selected from isopropyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, 1-fluoro-1-methylethyl, cyclopropyl, cyclobutyl, 1-fluorocyclopropyl, 2,2-difluorocyclopropyl and 2-fluorocyclopropyl. Preferably, the radical $R^{P'}$ carries 1, 2, 3 or 4 fluorine atoms.

Preferred compounds are also those in which Ar is 2- or 3-thienyl which may have 1, 2 or 3 of the aforementioned substituents. Examples thereof are 2,5-dichlorothien-3-yl and 5-chlorothien-2-yl.

$R^3$ is preferably hydrogen or $C_1$-$C_4$-alkyl, specifically methyl.

$R^4$ in $OR^4$ substituents is frequently H, $C_1$-$C_4$-alkyl, $CF_3$, $CHF_2$ or phenyl. $OR^4$ is particularly preferably methoxy, trifluoromethoxy or phenoxy.

$R^4$ in $COOR^4$ substituents is frequently H or $C_1$-$C_4$-alkyl. $COOR^4$ is particularly preferably $C_1$-$C_4$-alkoxycarbonyl such as methoxycarbonyl, ethoxycarbonyl, n-propoxycarbonyl, i-propoxycarbonyl, n-butoxycarbonyl or t-butoxycarbonyl.

In $CONR^5R^6$ substituents, $R^5$ is preferably H or $C_1$-$C_4$-alkyl and $R^6$ is preferably H, $C_1$-$C_4$-alkyl or $COR^9$. $CONR^5R^6$ is particularly preferably $CONH_2$, $CONHCH_3$, $CON(CH_3)_2$ or $CONHCOCH_3$.

In $NR^5R^6$ substituents, $R^5$ is preferably H, $C_1$-$C_4$-alkyl or phenyl-substituted $C_1$-$C_4$-alkyl and $R^6$ is H, $C_1$-$C_4$-alkyl or $COR^9$. $NR^5R^6$ is particularly preferably $NH_2$, $NHCH_3$, $N(CH_3)_2$, NH-benzyl or $NHCOCH_3$.

In $SO_2NR^5R^6$ substituents, $R^5$ is preferably H or $C_1$-$C_4$-alkyl and $R^6$ is preferably H, $C_1$-$C_4$-alkyl or $COR^9$. $SO_2NR^5R^6$ is particularly preferably sulfamoyl.

Where $R^5$, $R^6$ in the $NR^5R^6$, $CONR^5R^6$, $SO_2NR^5R^6$ substituents are, together with the nitrogen atom to which they are bonded, a 5- or 6-membered saturated or unsaturated N-heterocycle, the $NR^5R^6$ group in these radicals is, for example, N-pyrrolidinyl, N-piperidinyl, morpholin-1-yl or 4-methylpiperazin-1-yl.

$R^7$ in $SR^7$ substituents is preferably $C_1$-$C_4$-alkyl. $SR^7$ is particularly preferably thiomethyl.

$R^7$ in $SO_2R^7$ substituents is preferably H or $C_1$-$C_4$-alkyl. $SO_2R^7$ is particularly preferably methylsulfonyl.

$R^8$ in $COR^8$ substituents is preferably H, $C_1$-$C_4$-alkyl or phenyl. $COR^8$ is particularly preferably formyl, acetyl or benzoyl.

$R^9$ in $COR^9$ substituents is preferably H, $C_1$-$C_4$-alkyl or phenyl. $COR^9$ is particularly preferably formyl, acetyl or benzoyl.

$R^{10}$ in the $NR^{10}$ group is preferably hydrogen or methyl.

Particularly preferred compounds of the general formula I.A and I.B are the compounds of the formula I.A/B indicated below, in which $R^1$ has the meanings indicated above, $R^P$ has the meanings indicated previously, and Q is $CH_2$ or an N—$R^3$ group with the meanings indicated for $R^3$. Examples of such compounds are the compounds I.A/B-1 to I.A/B.135 in which $R^1$, Q and $R^p$ have the meanings indicated in each line in Table 1.

TABLE 1

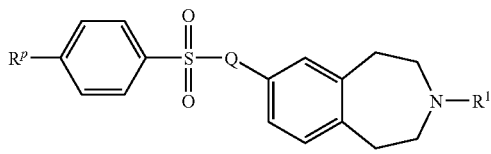

(I.A/B)

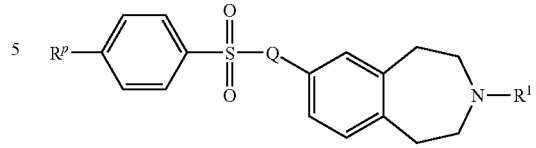

| | $R^1$ | Q | $R^p$ |
|---|---|---|---|
| 1 | Ethyl, | NH | $CH(CH_3)_2$ |
| 2 | n-Propyl | NH | $CH(CH_3)_2$ |
| 3 | $CH_2CF_3$ | NH | $CH(CH_3)_2$ |
| 4 | $CH_2CH_2CF_3$ | NH | $CH(CH_3)_2$ |
| 5 | Cyclopropylmethyl | NH | $CH(CH_3)_2$ |
| 6 | Propen-3-yl | NH | $CH(CH_3)_2$ |
| 7 | Propyn-3-yl | NH | $CH(CH_3)_2$ |
| 8 | $CH_2CH_2F$ | NH | $CH(CH_3)_2$ |
| 9 | $CH_2CH_2CH_2F$ | NH | $CH(CH_3)_2$ |
| 10 | Ethyl, | $N\text{-}CH_3$ | $CH(CH_3)_2$ |
| 11 | n-Propyl | $N\text{-}CH_3$ | $CH(CH_3)_2$ |
| 12 | $CH_2CF_3$ | $N\text{-}CH_3$ | $CH(CH_3)_2$ |
| 13 | $CH_2CH_2CF_3$ | $N\text{-}CH_3$ | $CH(CH_3)_2$ |
| 14 | Cyclopropylmethyl | $N\text{-}CH_3$ | $CH(CH_3)_2$ |
| 15 | Propen-3-yl | $N\text{-}CH_3$ | $CH(CH_3)_2$ |
| 16 | Propyn-3-yl | $N\text{-}CH_3$ | $CH(CH_3)_2$ |
| 17 | $CH_2CH_2F$ | $N\text{-}CH_3$ | $CH(CH_3)_2$ |
| 18 | $CH_2CH_2CH_2F$ | $N\text{-}CH_3$ | $CH(CH_3)_2$ |
| 19 | Ethyl, | NH | $CH_2CH_3$ |
| 20 | n-Propyl | NH | $CH_2CH_3$ |
| 21 | $CH_2CF_3$ | NH | $CH_2CH_3$ |
| 22 | $CH_2CH_2CF_3$ | NH | $CH_2CH_3$ |
| 23 | Cyclopropylmethyl | NH | $CH_2CH_3$ |
| 24 | Propen-3-yl | NH | $CH_2CH_3$ |
| 25 | Propyn-3-yl | NH | $CH_2CH_3$ |
| 26 | $CH_2CH_2F$ | NH | $CH_2CH_3$ |
| 27 | $CH_2CH_2CH_2F$ | NH | $CH_2CH_3$ |
| 28 | Ethyl, | $N\text{-}CH_3$ | $CH_2CH_3$ |
| 29 | n-Propyl | $N\text{-}CH_3$ | $CH_2CH_3$ |
| 30 | $CH_2CF_3$ | $N\text{-}CH_3$ | $CH_2CH_3$ |
| 31 | $CH_2CH_2CF_3$ | $N\text{-}CH_3$ | $CH_2CH_3$ |
| 32 | Cyclopropylmethyl | $N\text{-}CH_3$ | $CH_2CH_3$ |
| 33 | Propen-3-yl | $N\text{-}CH_3$ | $CH_2CH_3$ |
| 34 | Propyn-3-yl | $N\text{-}CH_3$ | $CH_2CH_3$ |
| 35 | $CH_2CH_2F$ | $N\text{-}CH_3$ | $CH_2CH_3$ |
| 36 | $CH_2CH_2CH_2F$ | $N\text{-}CH_3$ | $CH_2CH_3$ |
| 37 | Ethyl, | NH | $C(CH_3)_3$ |
| 38 | n-Propyl | NH | $C(CH_3)_3$ |
| 39 | $CH_2CF_3$ | NH | $C(CH_3)_3$ |
| 40 | $CH_2CH_2CF_3$ | NH | $C(CH_3)_3$ |
| 41 | Cyclopropylmethyl | NH | $C(CH_3)_3$ |
| 42 | Propen-3-yl | NH | $C(CH_3)_3$ |
| 43 | Propyn-3-yl | NH | $C(CH_3)_3$ |
| 44 | $CH_2CH_2F$ | NH | $C(CH_3)_3$ |
| 45 | $CH_2CH_2CH_2F$ | NH | $C(CH_3)_3$ |
| 46 | Ethyl, | $N\text{-}CH_3$ | $C(CH_3)_3$ |
| 47 | n-Propyl | $N\text{-}CH_3$ | $C(CH_3)_3$ |
| 48 | $CH_2CF_3$ | $N\text{-}CH_3$ | $C(CH_3)_3$ |
| 49 | $CH_2CH_2CF_3$ | $N\text{-}CH_3$ | $C(CH_3)_3$ |
| 50 | Cyclopropylmethyl | $N\text{-}CH_3$ | $C(CH_3)_3$ |
| 51 | Propen-3-yl | $N\text{-}CH_3$ | $C(CH_3)_3$ |
| 52 | Propyn-3-yl | $N\text{-}CH_3$ | $C(CH_3)_3$ |
| 53 | $CH_2CH_2F$ | $N\text{-}CH_3$ | $C(CH_3)_3$ |
| 54 | $CH_2CH_2CH_2F$ | $N\text{-}CH_3$ | $C(CH_3)_3$ |
| 55 | Ethyl, | NH | $CH=CH_2$ |
| 56 | n-Propyl | NH | $CH=CH_2$ |
| 57 | $CH_2CF_3$ | NH | $CH=CH_2$ |
| 58 | $CH_2CH_2CF_3$ | NH | $CH=CH_2$ |
| 59 | Cyclopropylmethyl | NH | $CH=CH_2$ |
| 60 | Propen-3-yl | NH | $CH=CH_2$ |
| 61 | Propyn-3-yl | NH | $CH=CH_2$ |
| 62 | $CH_2CH_2F$ | NH | $CH=CH_2$ |
| 63 | $CH_2CH_2CH_2F$ | NH | $CH=CH_2$ |
| 64 | Ethyl, | $N\text{-}CH_3$ | $CH=CH_2$ |
| 65 | n-Propyl | $N\text{-}CH_3$ | $CH=CH_2$ |
| 66 | $CH_2CF_3$ | $N\text{-}CH_3$ | $CH=CH_2$ |
| 67 | $CH_2CH_2CF_3$ | $N\text{-}CH_3$ | $CH=CH_2$ |
| 68 | Cyclopropylmethyl | $N\text{-}CH_3$ | $CH=CH_2$ |
| 69 | Propen-3-yl | $N\text{-}CH_3$ | $CH=CH_2$ |
| 70 | Propyn-3-yl | $N\text{-}CH_3$ | $CH=CH_2$ |
| 71 | $CH_2CH_2F$ | $N\text{-}CH_3$ | $CH=CH_2$ |
| 72 | $CH_2CH_2CH_2F$ | $N\text{-}CH_3$ | $CH=CH_2$ |
| 73 | Ethyl, | NH | $CF_3$ |
| 74 | n-Propyl | NH | $CF_3$ |
| 75 | $CH_2CF_3$ | NH | $CF_3$ |
| 76 | $CH_2CH_2CF_3$ | NH | $CF_3$ |
| 77 | Cyclopropylmethyl | NH | $CF_3$ |
| 78 | Propen-3-yl | NH | $CF_3$ |
| 79 | Propyn-3-yl | NH | $CF_3$ |
| 80 | $CH_2CH_2F$ | NH | $CF_3$ |
| 81 | $CH_2CH_2CH_2F$ | NH | $CF_3$ |
| 82 | Ethyl, | $N\text{-}CH_3$ | $CF_3$ |
| 83 | n-Propyl | $N\text{-}CH_3$ | $CF_3$ |
| 84 | $CH_2CF_3$ | $N\text{-}CH_3$ | $CF_3$ |
| 85 | $CH_2CH_2CF_3$ | $N\text{-}CH_3$ | $CF_3$ |
| 86 | Cyclopropylmethyl | $N\text{-}CH_3$ | $CF_3$ |
| 87 | Propen-3-yl | $N\text{-}CH_3$ | $CF_3$ |
| 88 | Propyn-3-yl | $N\text{-}CH_3$ | $CF_3$ |
| 89 | $CH_2CH_2F$ | $N\text{-}CH_3$ | $CF_3$ |
| 90 | $CH_2CH_2CH_2F$ | $N\text{-}CH_3$ | $CF_3$ |
| 91 | Ethyl, | $CH_2$ | $CH(CH_3)_2$ |
| 92 | n-Propyl | $CH_2$ | $CH(CH_3)_2$ |
| 93 | $CH_2CF_3$ | $CH_2$ | $CH(CH_3)_2$ |
| 94 | $CH_2CH_2CF_3$ | $CH_2$ | $CH(CH_3)_2$ |
| 95 | Cyclopropylmethyl | $CH_2$ | $CH(CH_3)_2$ |
| 96 | Propen-3-yl | $CH_2$ | $CH(CH_3)_2$ |
| 97 | Propyn-3-yl | $CH_2$ | $CH(CH_3)_2$ |
| 98 | $CH_2CH_2F$ | $CH_2$ | $CH(CH_3)_2$ |
| 99 | $CH_2CH_2CH_2F$ | $CH_2$ | $CH(CH_3)_2$ |
| 100 | Ethyl, | $CH_2$ | $CH_2CH_3$ |
| 101 | n-Propyl | $CH_2$ | $CH_2CH_3$ |
| 102 | $CH_2CF_3$ | $CH_2$ | $CH_2CH_3$ |
| 103 | $CH_2CH_2CF_3$ | $CH_2$ | $CH_2CH_3$ |
| 104 | Cyclopropylmethyl | $CH_2$ | $CH_2CH_3$ |
| 105 | Propen-3-yl | $CH_2$ | $CH_2CH_3$ |
| 106 | Propyn-3-yl | $CH_2$ | $CH_2CH_3$ |
| 107 | $CH_2CH_2F$ | $CH_2$ | $CH_2CH_3$ |
| 108 | $CH_2CH_2CH_2F$ | $CH_2$ | $CH_2CH_3$ |
| 109 | Ethyl, | $CH_2$ | $C(CH_3)_3$ |
| 110 | n-Propyl | $CH_2$ | $C(CH_3)_3$ |
| 111 | $CH_2CF_3$ | $CH_2$ | $C(CH_3)_3$ |
| 112 | $CH_2CH_2CF_3$ | $CH_2$ | $C(CH_3)_3$ |
| 113 | Cyclopropylmethyl | $CH_2$ | $C(CH_3)_3$ |
| 114 | Propen-3-yl | $CH_2$ | $C(CH_3)_3$ |
| 115 | Propyn-3-yl | $CH_2$ | $C(CH_3)_3$ |
| 116 | $CH_2CH_2F$ | $CH_2$ | $C(CH_3)_3$ |
| 117 | $CH_2CH_2CH_2F$ | $CH_2$ | $C(CH_3)_3$ |
| 118 | Ethyl, | $CH_2$ | $CH=CH_2$ |
| 119 | n-Propyl | $CH_2$ | $CH=CH_2$ |
| 120 | $CH_2CF_3$ | $CH_2$ | $CH=CH_2$ |
| 121 | $CH_2CH_2CF_3$ | $CH_2$ | $CH=CH_2$ |
| 122 | Cyclopropylmethyl | $CH_2$ | $CH=CH_2$ |
| 123 | Propen-3-yl | $CH_2$ | $CH=CH_2$ |
| 124 | Propyn-3-yl | $CH_2$ | $CH=CH_2$ |
| 125 | $CH_2CH_2F$ | $CH_2$ | $CH=CH_2$ |
| 126 | $CH_2CH_2CH_2F$ | $CH_2$ | $CH=CH_2$ |
| 127 | Ethyl, | $CH_2$ | $CF_3$ |
| 128 | n-Propyl | $CH_2$ | $CF_3$ |
| 129 | $CH_2CF_3$ | $CH_2$ | $CF_3$ |
| 130 | $CH_2CH_2CF_3$ | $CH_2$ | $CF_3$ |
| 131 | Cyclopropylmethyl | $CH_2$ | $CF_3$ |
| 132 | Propen-3-yl | $CH_2$ | $CF_3$ |
| 133 | Propyn-3-yl | $CH_2$ | $CF_3$ |

TABLE 1-continued

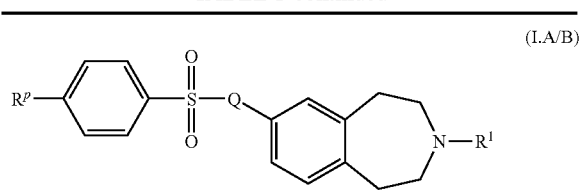
(I.A/B)

| | R[1] | Q | R[p] |
|---|---|---|---|
| 134 | CH$_2$CH$_2$F | CH$_2$ | CF$_3$ |
| 135 | CH$_2$CH$_2$CH$_2$F | CH$_2$ | CF$_3$ |
| 136 | Ethyl, | NH | CH(CH$_3$)CH$_2$F |
| 137 | n-Propyl | NH | CH(CH$_3$)CH$_2$F |
| 138 | CH$_2$CF$_3$ | NH | CH(CH$_3$)CH$_2$F |
| 139 | CH$_2$CH$_2$CF$_3$ | NH | CH(CH$_3$)CH$_2$F |
| 140 | CyclopropylmethYl | NH | CH(CH$_3$)CH$_2$F |
| 141 | Propen-3-yl | NH | CH(CH$_3$)CH$_2$F |
| 142 | Propyn-3-yl | NH | CH(CH$_3$)CH$_2$F |
| 143 | CH$_2$CH$_2$F | NH | CH(CH$_3$)CH$_2$F |
| 144 | CH$_2$CH$_2$CH$_2$F | NH | CH(CH$_3$)CH$_2$F |
| 145 | Ethyl, | N-CH$_3$ | CH(CH$_3$)CH$_2$F |
| 146 | n-Propyl | N-CH$_3$ | CH(CH$_3$)CH$_2$F |
| 147 | CH$_2$CF$_3$ | N-CH$_3$ | CH(CH$_3$)CH$_2$F |
| 148 | CH$_2$CH$_2$CF$_3$ | N-CH$_3$ | CH(CH$_3$)CH$_2$F |
| 149 | Cyclopropylmethyl | N-CH$_3$ | CH(CH$_3$)CH$_2$F |
| 150 | Propen-3-yl | N-CH$_3$ | CH(CH$_3$)CH$_2$F |
| 151 | Propyn-3-yl | N-CH$_3$ | CH(CH$_3$)CH$_2$F |
| 152 | CH$_2$CH$_2$F | N-CH$_3$ | CH(CH$_3$)CH$_2$F |
| 153 | CH$_2$CH$_2$CH$_2$F | N-CH$_3$ | CH(CH$_3$)CH$_2$F |
| 154 | Ethyl, | NH | CH(CH$_2$F)$_2$ |
| 155 | n-Propyl | NH | CH(CH$_2$F)$_2$ |
| 156 | CH$_2$CF$_3$ | NH | CH(CH$_2$F)$_2$ |
| 157 | CH$_2$CH$_2$CF$_3$ | NH | CH(CH$_2$F)$_2$ |
| 158 | Cyclopropylmethyl | NH | CH(CH$_2$F)$_2$ |
| 159 | Propen-3-yl | NH | CH(CH$_2$F)$_2$ |
| 160 | Propyn-3-yl | NH | CH(CH$_2$F)$_2$ |
| 161 | CH$_2$CH$_2$F | NH | CH(CH$_2$F)$_2$ |
| 162 | CH$_2$CH$_2$CH$_2$F | NH | CH(CH$_2$F)$_2$ |
| 163 | Ethyl, | N-CH$_3$ | CH(CH$_2$F)$_2$ |
| 164 | n-Propyl | N-CH$_3$ | CH(CH$_2$F)$_2$ |
| 165 | CH$_2$CF$_3$ | N-CH$_3$ | CH(CH$_2$F)$_2$ |
| 166 | CH$_2$CH$_2$CF$_3$ | N-CH$_3$ | CH(CH$_2$F)$_2$ |
| 167 | Cyclopropylmethyl | N-CH$_3$ | CH(CH$_2$F)$_2$ |
| 168 | Propen-3-yl | N-CH$_3$ | CH(CH$_2$F)$_2$ |
| 169 | Propyn-3-yl | N-CH$_3$ | CH(CH$_2$F)$_2$ |
| 170 | CH$_2$CH$_2$F | N-CH$_3$ | CH(CH$_2$F)$_2$ |
| 171 | CH$_2$CH$_2$CH$_2$F | N-CH$_3$ | CH(CH$_2$F)$_2$ |
| 172 | Ethyl, | NH | CF(CH$_3$)$_2$ |
| 173 | n-Propyl | NH | CF(CH$_3$)$_2$ |
| 174 | CH$_2$CF$_3$ | NH | CF(CH$_3$)$_2$ |
| 175 | CH$_2$CH$_2$CF$_3$ | NH | CF(CH$_3$)$_2$ |
| 176 | Cyclopropylmethyl | NH | CF(CH$_3$)$_2$ |
| 177 | Propen-3-yl | NH | CF(CH$_3$)$_2$ |
| 178 | Propyn-3-yl | NH | CF(CH$_3$)$_2$ |
| 179 | CH$_2$CH$_2$F | NH | CF(CH$_3$)$_2$ |
| 180 | CH$_2$CH$_2$CH$_2$F | NH | CF(CH$_3$)$_2$ |
| 181 | Ethyl, | N-CH$_3$ | CF(CH$_3$)$_2$ |
| 182 | n-Propyl | N-CH$_3$ | CF(CH$_3$)$_2$ |
| 183 | CH$_2$CF$_3$ | N-CH$_3$ | CF(CH$_3$)$_2$ |
| 184 | CH$_2$CH$_2$CF$_3$ | N-CH$_3$ | CF(CH$_3$)$_2$ |
| 185 | Cyclopropylmethyl | N-CH$_3$ | CF(CH$_3$)$_2$ |
| 186 | Propen-3-yl | N-CH$_3$ | CF(CH$_3$)$_2$ |
| 187 | Propyn-3-yl | N-CH$_3$ | CF(CH$_3$)$_2$ |
| 188 | CH$_2$CH$_2$F | N-CH$_3$ | CF(CH$_3$)$_2$ |
| 189 | CH$_2$CH$_2$CH$_2$F | N-CH$_3$ | CF(CH$_3$)$_2$ |
| 190 | Ethyl, | NH | CH$_2$CHF$_2$ |
| 191 | n-Propyl | NH | CH$_2$CHF$_2$ |
| 192 | CH$_2$CF$_3$ | NH | CH$_2$CHF$_2$ |
| 193 | CH$_2$CH$_2$CF$_3$ | NH | CH$_2$CHF$_2$ |
| 194 | Cyclopropylmethyl | NH | CH$_2$CHF$_2$ |
| 195 | Propen-3-yl | NH | CH$_2$CHF$_2$ |
| 196 | Propyn-3-yl | NH | CH$_2$CHF$_2$ |
| 197 | CH$_2$CH$_2$F | NH | CH$_2$CHF$_2$ |
| 198 | CH$_2$CH$_2$CH$_2$F | NH | CH$_2$CHF$_2$ |
| 199 | Ethyl, | N-CH$_3$ | CH$_2$CHF$_2$ |
| 200 | n-Propyl | N-CH$_3$ | CH$_2$CHF$_2$ |
| 201 | CH$_2$CF$_3$ | N-CH$_3$ | CH$_2$CHF$_2$ |
| 202 | CH$_2$CH$_2$CF$_3$ | N-CH$_3$ | CH$_2$CHF$_2$ |

TABLE 1-continued

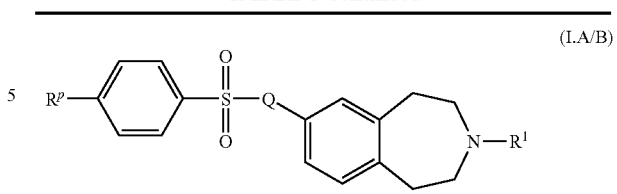
(I.A/B)

| | R[1] | Q | R[p] |
|---|---|---|---|
| 203 | Cyclopropylmethyl | N-CH$_3$ | CH$_2$CHF$_2$ |
| 204 | Propen-3-yl | N-CH$_3$ | CH$_2$CHF$_2$ |
| 205 | Propyn-3-yl | N-CH$_3$ | CH$_2$CHF$_2$ |
| 206 | CH$_2$CH$_2$F | N-CH$_3$ | CH$_2$CHF$_2$ |
| 207 | CH$_2$CH$_2$CH$_2$F | N-CH$_3$ | CH$_2$CHF$_2$ |
| 208 | Ethyl, | NH | c-CF(CH$_2$CH$_2$) |
| 209 | n-Propyl | NH | c-CF(CH$_2$CH$_2$) |
| 210 | CH$_2$CF$_3$ | NH | c-CF(CH$_2$CH$_2$) |
| 211 | CH$_2$CH$_2$CF$_3$ | NH | c-CF(CH$_2$CH$_2$) |
| 212 | Cyclopropylmethyl | NH | c-CF(CH$_2$CH$_2$) |
| 213 | Propen-3-yl | NH | c-CF(CH$_2$CH$_2$) |
| 214 | Propyn-3-yl | NH | c-CF(CH$_2$CH$_2$) |
| 215 | CH$_2$CH$_2$F | NH | c-CF(CH$_2$CH$_2$) |
| 216 | CH$_2$CH$_2$CH$_2$F | NH | c-CF(CH$_2$CH$_2$) |
| 217 | Ethyl, | N-CH$_3$ | c-CF(CH$_2$CH$_2$) |
| 218 | n-Propyl | N-CH$_3$ | c-CF(CH$_2$CH$_2$) |
| 219 | CH$_2$CF$_3$ | N-CH$_3$ | c-CF(CH$_2$CH$_2$) |
| 220 | CH$_2$CH$_2$CF$_3$ | N-CH$_3$ | c-CF(CH$_2$CH$_2$) |
| 221 | Cyclopropylmethyl | N-CH$_3$ | c-CF(CH$_2$CH$_2$) |
| 222 | Propen-3-yl | N-CH$_3$ | c-CF(CH$_2$CH$_2$) |
| 223 | Propyn-3-yl | N-CH$_3$ | c-CF(CH$_2$CH$_2$) |
| 224 | CH$_2$CH$_2$F | N-CH$_3$ | c-CF(CH$_2$CH$_2$) |
| 225 | CH$_2$CH$_2$CH$_2$F | N-CH$_3$ | c-CF(CH$_2$CH$_2$) | c = cyclo

Particularly preferred compounds of the general formula I.C and I.D are the compounds of the formula I.C/D indicated below, in which R[1] has the meanings indicated above, R[P] has the meanings indicated previously, and Q is CH$_2$ or an N—R[3] group with the meanings indicated for R[3]. Examples of such compounds are the compounds I.C/D-1 to I.C/D.135 in which R[1], Q and R[P] have the meanings indicated in each line in Table 1.

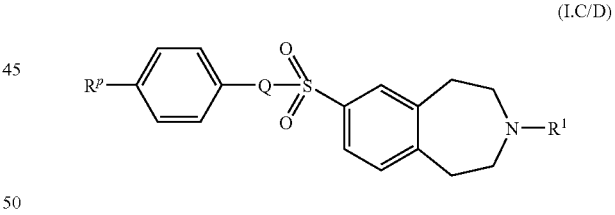
(I.C/D)

The compounds of the invention can be prepared by analogy to the preparation of known 2,3,4,5-tetrahydrobenzo[c]-1H-azepines. The methods of preparation are explained in the following schemes:

Compound I.A can be prepared for example by the process shown in Scheme 1:

Scheme 1:

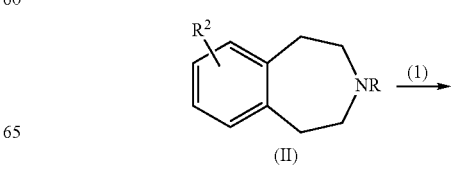

(II)

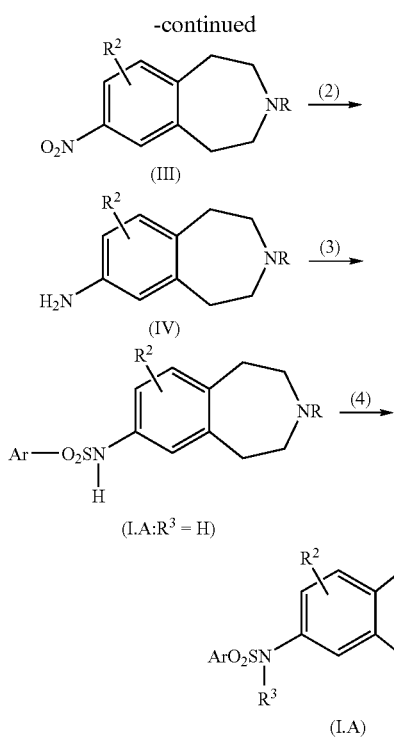

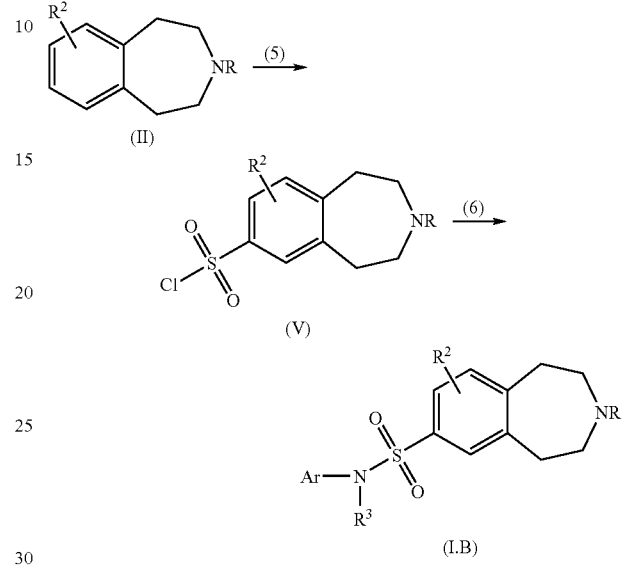

In Scheme 1, R has the meanings different from hydrogen indicated for $R^1$. As shown in Scheme 1, in a first step (1) there is nitration of a 2,3,4,5-tetrahydrobenzo[c]-1H-azepine II substituted on the nitrogen. The nitration is based on that indicated in J. Heterocycl. Chem. 1979, 16, 1525. The 7-nitro-2,3,4,5-tetrahydrobenzo[c]-1H-azepine III obtained thereby is converted in step (2) by reduction by known processes (see, for example, J. Heterocycl. Chem. 1979, 16, 1525) into the 7-amino-2,3,4,5-tetrahydrobenzo[c]-1H-azepine IV. Compound IV is reacted in step (3) with an arylsulfonyl halide (e.g. according to Synthesis 1997, 895), resulting in the compound I.A with $R^3$=H and $R^1 \neq H$. Compound I.A with $R^3$=H can then be converted in a manner known per se into the compounds I.A with $R^3 \neq H$, e.g. by acylation into compounds I.A with $R^3$=$C_1$-$C_4$-alkylcarbonyl or phenylcarbonyl or by alkylation into compounds with $R^3$=$C_1$-$C_4$-alkyl or phenyl-$C_1$-$C_4$-alkyl (see, for example, Tetrahedron, 2000, 56, 7553).

The compound I.B can be prepared for example by the process shown in Scheme 2:

In Scheme 2, R has the meanings different from hydrogen indicated for $R^1$. As shown in Scheme 2, firstly a substituted tetrahydrobenzazepine II is subjected to a sulfochlorination under conditions usual per se, e.g. the conditions indicated in J. Med. Chem. 1999, 42, 3315. The 7-chlorosulfonyl-2,3,4,5-tetrahydrobenzo[c]-1H-azepine V obtained in this way is then reacted with a (hetero)aromatic amine Ar—NH—$R^3$, resulting in the compound I.B. (see J. Med. Chem. 2000, 43, 4363). If the chlorosulfonyl compound V is reacted with a primary heteroaromatic amine Ar—$NH_2$, it is subsequently possible to introduce the group $R^3$ in a manner known per se, as set forth in Scheme 1.

The compound I.B can be prepared for example by the process shown in Scheme 3:

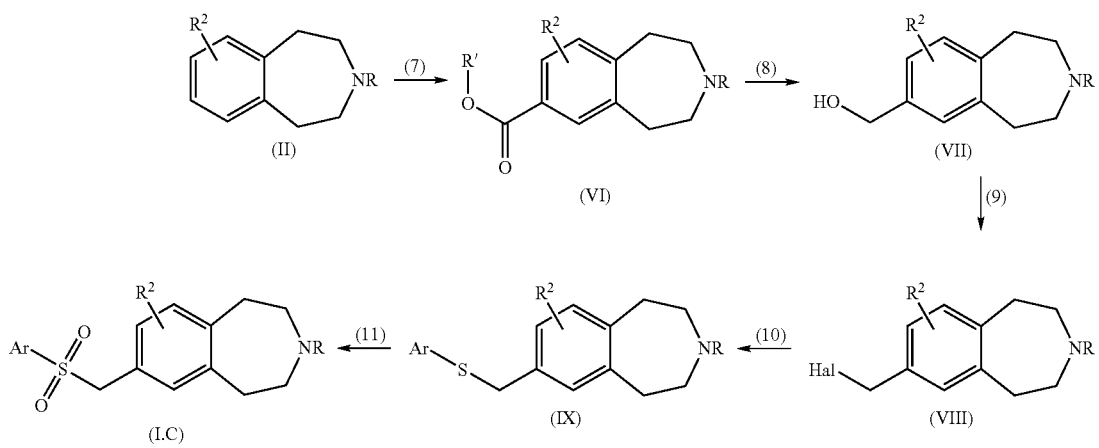

In Scheme 3, R has the meanings different from hydrogen indicated for $R^1$. R' is an alkyl group having 1 to 4 C atoms, e.g. methyl or ethyl, Hal is chlorine or bromine. The compound I.B is prepared for example by firstly introducing a halomethyl group into the N-substituted benzazepine II (steps 7 to 9), subsequently reacting the halomethyl compound VIII obtained in this way with a (het)arylmercaptan Ar—SH by known processes (see Tetrahedron 2002, 58, 9879) (step 10), and oxidizing the compound IX obtained thereby to the sulfone by known processes as set forth, for example, in J. Med. Chem. 2003, 46, 3021 (step 11). The halomethyl group in VIII is assembled for example by introducing an alkoxycarbonyl group into a substituted benzazepine II by reaction with oxalyl chloride by the method described in European Journal of Organic Chemistry 2002, 2298 (step 7). The alkoxycarbonyl group in VI can then be converted into a hydroxymethyl group in a manner known per se by reaction with suitable reducing agents, e.g. lithium aluminum hydride (step 8). The hydroxymethyl compound VII obtained thereby can then be converted into the halomethyl compound VIII by treatment with suitable halogenating agents, e.g. with thionyl chloride, phosphoryl chloride, phosphorus trichloride or phosphorus tribromide, where appropriate in the presence of a base, e.g. a tertiary amine or pyridine.

The compounds I.D can be prepared by the method depicted in Scheme 4:

Scheme 4:

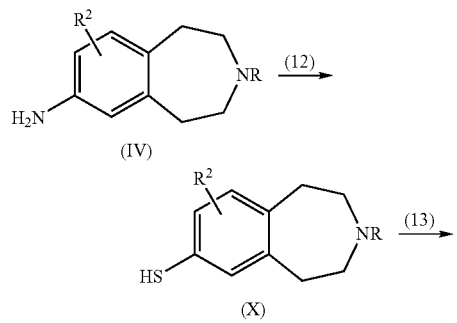

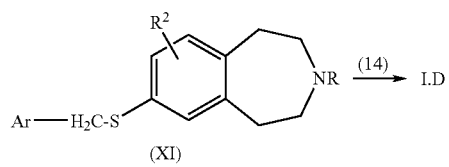

In Scheme 4, $R^2$ and Ar have the aforementioned meanings and R has one of the meanings mentioned for $R^1$ or is a protective group. I.C is prepared for example by diazotizing the amine IV (see Scheme 1) and then converting into the mercaptan of the formula X by treatment with $H_2S$ or alkali metal sulfite (step 12). Processes for doing this are known (e.g. from Houben, Weyl, Methoden der Organischen Chemie, vol. E11, pages 43 and 176, and J. March 3rd edition 1985, pages 601 et seq. and literature cited therein) and can be applied here analogously. The mercaptan X is then reacted with a compound Ar—$CH_2$-Hal (Hal=halogen, in particular chlorine, bromine or iodine) under conditions known per se, resulting in the thioether XI (step 13). Subsequent oxidation of the thioether to the sulfone I.D (step 14) can take place in a manner known per se, e.g. in analogy to step 11 in Scheme 3.

Compounds I with $R^1$=H are prepared in analogy to the processes depicted in Schemes 1 to 4, by providing the nitrogen of the benzazepine IIa with a protective group, subsequently assembling the group Ar—Y—$SO_2$—B-A by the processes depicted in Schemes 1 to 4, and subsequently removing the protective group again. The azepine nitrogen in the compound I with $R^1$=H, obtained thereby, is then available for further reactions. This procedure is depicted by way of example for the trifluoroacetyl protective group in Scheme 5.

Scheme 5

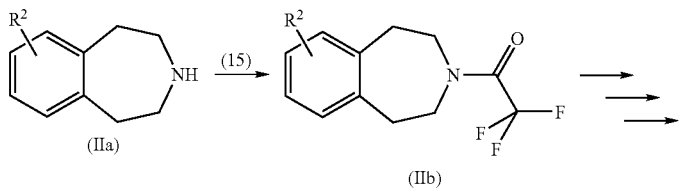

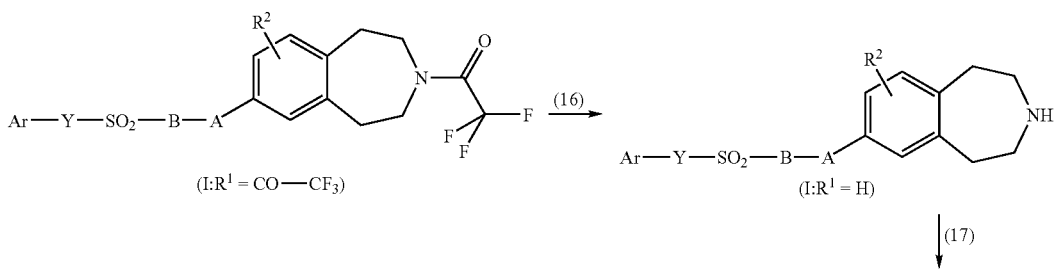

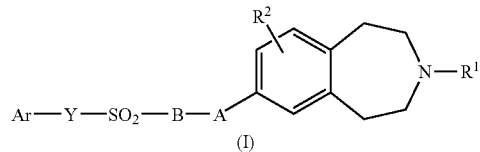

(I)

In step 15, the benzazepine IIa is reacted with, for example, trifluoroacetic anhydride by the method described in Synth. Commun. 1986, 16, 267, resulting in the trifluoroacetyl-protected benzazepine IIb. Compound IIb is then converted by the processes described in Schemes 1 to 4 into the compound of the formula I' in which Ar, Y, B and A have the aforementioned meanings. The compound I with $R^1$=COCF$_3$ is subsequently deprotected (step 16), for example by treating it with alkali metal carbonate, e.g. potassium carbonate, in a water/alcohol mixture, e.g. a water/methanol mixture, by the method described in J. Org. Chem. 1999, 64, 6724. The compound I with $R^1$=H can then be converted into the compound 1 with $R^1 \ne H$ in step 17 by standard processes, e.g. by alkylation with compounds $R^1$-Hal in which Hal is chlorine, bromine or iodine, and $R^1$ is optionally substituted alkyl, haloalkyl, cycloalkyl or the like. Particularly preferred compounds I with $R^1$=CH$_2$—$R^{1'}$ can be prepared by reacting an aldehyde of the formula $R^{1'}$—CHO in the presence of a reducing agent with the compound I with $R^1$=H in a reductive amination, e.g. by the process described in J. Med. Chem. 1992, 35, 4315.

The preparation of the benzazepines II and IIa is known from the prior art or can take place in analogy to known processes, e.g. by the method depicted in Scheme 6. In Scheme 6, R is alkyl having 1 to 4 C atoms, in particular methyl or ethyl. X is a nucleophilically displaceable leaving group, e.g. Br, tosylate or, in particular, mesylate. $R^1$ has the previous meanings different from hydrogen.

Reaction of the compound XV obtained in this way with a primary amine $R^1$=NH$_2$ or with ammonia by the method described in J. Med. Chem. 2000, 43, 3653 then leads to the substituted benzazepine II or IIa.

Unless indicated otherwise, the reactions described above are generally carried out in a solvent at temperatures between room temperature and the boiling point of the solvent used. Alternatively, the energy of activation necessary for the reaction can also be introduced into the reaction mixture by means of microwaves, which has proved particularly suitable in the case of reactions catalyzed by transition metals (see Tetrahedron 2001, 57, pages 9199 et seq., pages 9225 et seq. for reactions using microwaves, and in general "Microwaves in Organic Synthesis", André Loupy (Ed.), Wiley-VCH 2002.

Examples of solvents which can be used are ethers such as diethyl ether, diisopropyl ether, methyl tert-butyl ether or tetrahydrofuran, aprotic polar solvents such as dimethylformamide, dimethyl sulfoxide, dimethoxyethane and acetonitrile, aromatic hydrocarbons such as toluene, xylene, ketones such as acetone or methyl ethyl ketone, halohydrocarbons such as dichloromethane, trichloromethane, dichloroethane, esters such as ethyl acetate, methyl butyrate, carboxylic acids such as acetic acid or propionic acid, and alcohols such as methanol, ethanol, n-propanol, isopropanol or butanol.

If desired, a base is present to neutralize protons liberated in the reactions. Suitable bases include inorganic bases such as sodium or potassium carbonate, sodium or potassium

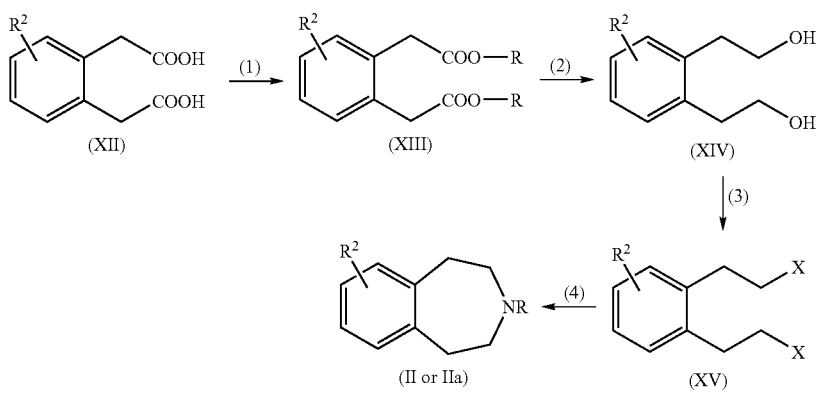

For this purpose, a phenylenediacetic acid derivative of the formula XII is converted in a manner known per se into the dialkyl ester XI, e.g. into the dimethyl ester (see, for example, Tetrahedron 1989, 45, 4969). The latter can be reduced in a manner known per se to the diol XIV, e.g. with lithium aluminum hydride by the method described in European Journal of Organic Chemistry, 2000, 3527. The OH groups in the diol XIV obtained in this way are then converted into leaving groups X such as Br, tosylate or, in particular, mesylate, e.g. by the method described in J. Org. Chem. 1997, 62, 5982.

bicarbonate, also alcoholates such as sodium methoxide, sodium ethoxide, alkali metal hydrides such as sodium hydride, and organometallic compounds such as butyllithium or alkylmagnesium compounds, or organic nitrogen bases such as triethylamine or pyridine. The latter may serve as solvent at the same time.

The crude product is isolated in a conventional way, for example by filtering, distilling off the solvent or extracting from the reaction mixture etc. The resulting compounds can be purified in a conventional way, for example by recrystalization from a solvent, chromatography or conversion into an acid addition salt.

The acid addition salts are prepared in a conventional way by mixing the free base with the appropriate acid, where appropriate in solution in an organic solvent, for example a lower alcohol such as methanol, ethanol or propanol, an ether such as methyl tert-butyl ether, diisopropyl ether, a ketone such as acetone or methyl ethyl ketone or an ester such as ethyl acetate.

The compounds of the invention of the formula I are highly selective dopamine $D_3$ receptor ligands which, because of their low affinity for other receptors such as $D_1$ receptors, $D_4$ receptors, $\alpha 1$- and/or $\alpha 2$-adrenergic receptors, muskarinergic receptors, histaminic receptors, opiate receptors and, in particular, for dopamine $D_2$ receptors, have fewer side effects than classical neuroleptic agents which are $D_2$ receptor antagonists.

The high affinity of the compounds of the invention for $D_3$ receptors is reflected in very low in vitro $K_i$ values of usually less than 100 nM (nmol/l), in particular less than 50 nM, especially less than 10 nM, more preferably less than 5 nM. Binding affinities for $D_3$ receptors can be determined for example in receptor binding studies via the displacement of [$^{125}$I]-iodosulpride.

The selectivity $K_i(D_2)/K_i(D_3)$ of the compounds of the invention is usually at least 10, preferably at least 30, even better at least 50 and particularly advantageously at least 100. Receptor binding studies on $D_1$, $D_2$ and $D_4$ receptors can be carried out for example via the displacement of [$^3$H] SCH23390, [$^{125}$I]iodosulpride or [$^{125}$I]spiperone.

The compounds can, because of their binding profile, be used for the treatment of disorders which respond to dopamine $D_3$ ligands, i.e. they are effective for the treatment of disturbances and disorders in which influencing (modulation) of dopamine $D_3$ receptors leads to an improvement in the clinical picture or to cure of the disease. Examples of disorders of this type are disturbances or disorders of the central nervous system.

Disturbances or disorders of the central nervous system mean disturbances which effect the spinal cord and, in particular, the brain. The term "disturbance" in the sense according to the invention refers to abnormalities which are usually recurrent as pathological states or functions that may reveal themselves in the form of certain signs, symptoms and/or dysfunctions. The treatment according to the invention may be directed at individual disturbances, i.e. abnormalities or pathological states, but it is also possible for a plurality of abnormalities, which are causally connected together where appropriate, to be combined into patterns, i.e. syndromes, which can be treated according to the invention.

The disturbances which can be treated according to the invention include in particular psychiatric and neurological disturbances. These include in particular organic disturbances, symptomatic disturbances included, such as psychoses of the acute exogenous type or associated psychoses with an organic or exogenous cause, e.g. associated with metabolic disturbances, infections and endocrinopathies; endogenous psychoses such as schizophrenia, and schizotypal and delusional disorders; affective disorders such as depressions, mania and manic-depressive states; and combined forms of the disorders described above; neurotic and somatoform disorders, and disorders associated with stress; dissociative disorders, e.g. deficits, cloudings and splittings of consciousness and personality disorders; disorders of attention and waking/sleeping behavior, such as behavioral disturbances and emotional disturbances starting in childhood and adolescence, such as hyperactivity in children, intellectual deficits, especially attention deficit disorders, disturbances of memory and cognition, e.g. learning and memory impairments (impaired cognitive function), dementia, narcolepsy and sleep disorders, e.g. restless legs syndrome; developmental disturbances; anxiety states; delirium; disorders of the sex life, e.g. male impotence; eating disorders, e.g. anorexia or bulimia; addiction; and other undefined psychiatric disorders.

The disorders which can be treated according to the invention also include Parkinsonism and epilepsy and, in particular, the affective disorders associated therewith.

Addictive disorders include the psychological disorders and behavioral disturbances caused by abuse of psychotropic substances such as pharmaceuticals or drugs, and other addictive disorders such as, for example, compulsive gambling (impulse control disorders not elsewhere classified). Examples of addictive substances are: opiods (e.g. morphine, heroin, codeine); cocaine; nicotine; alcohol; substances which interact with the GABA chloride channel complex, sedatives, hypnotics or tranquilizers, for example benzodiazepines; LSD; cannabinoids; psychomotor stimulants such as 3,4-methylenedioxy-N-methylamphetamine (ecstasy); amphetamine and amphetamine-like substances such as methylphenidate or other stimulants including caffeine. Addictive substances requiring particular attention are opioids, cocaine, amphetamine or amphetamine-like substances, nicotine and alcohol.

With a view to the treatment of addictive disorders, the compounds of the invention of the formula I which are particularly preferred are those which themselves have no psychotropic effect. This can also be observed in a test on rats which reduce self-administration of psychotropic substances, for example cocaine, after administration of compounds which can be used according to the invention.

According to a further aspect of the present invention, the compounds of the invention are suitable for the treatment of disorders the causes of which can at least in part be attributed to an abnormal activity of dopamine $D_3$ receptors.

According to another aspect of the present invention, the treatment is directed in particular at those disorders which can be influenced by a binding of, preferably exogenously added, binding partners (ligands) to dopamine $D_3$ receptors in the sense of an expedient medical treatment.

The disorders which can be treated with the compounds of the invention are frequently characterized by a progressive development, i.e. the states described above change over the course of time, the severity usually increasing and, where appropriate, states possibly interchanging or other states being added to previously existing states.

The compounds of the invention can be used to treat a large number of signs, symptoms and/or dysfunctions associated with the disorders of the central nervous system and, in particular, the aforementioned states. These include for example an impaired relation to reality, lack of insight and the ability to comply with the usual social norms and demands of life, changes in behavior, changes in individual urges such as hunger, sleep, thirst, etc. and in mood, disorders of memory and association, personality changes, especially emotional lability, hallucinations, ego disturbances, incoherence of thought, ambivalence, autism, depersonalization or hallucinations, delusional ideas, staccato speech, absence of sinekinesis, small-step gait, bent posture of trunk and limbs, tremor, mask-like face, monotonous speech, depression, apathy, deficient spontaneity and irresolution, reduced association ability, anxiety, nervous agitation, stammering, social phobia, panic disorders, withdrawal syndromes associated with dependence, expansive syndromes, states of agitation and confusion, dysphoria, dyskinetic syndromes and tic disorders, e.g. associated with Huntington's chorea, Gilles-de-la-Tourette syndrome, vertigo syndromes, e.g. peripheral postural, rotational and vestibular vertigo, melancholia, hysteria, hypochondria and the like.

A treatment in the sense according to the invention includes not only the treatment of acute or chronic signs, symptoms and/or dysfunctions but also a preventive treatment (prophylaxis), in particular as recurrence or episode prophylaxis. The treatment may be symptomatic, for example directed at suppression of symptoms. It may take place short-term, be directed at the medium term or may also be a long-term treatment, for example as part of maintenance therapy.

The compounds of the invention are preferably suitable for the treatment of disorders of the central nervous system, in particular for the treatment of affective disorders; neurotic disorders, stress disorders and somatoform disorders and psychoses and specifically for the treatment of schizophrenia and depression. Owing to their high selectivity for the $D_3$ receptor, the compounds I of the invention are also for the treatment of renal function disorders, especially of renal function disorders caused by diabetes mellitus (see WO 00/67847) and specifically of diabetic nephropathy.

The use according to the invention of the described compounds comprises a method within the scope of the treatment. This entails the individual to be treated, preferably a mammal, in particular a human or agricultural or domestic animal being given an effective amount of one or more compounds, usually formulated in accordance with pharmaceutical and veterinary practice. Whether such a treatment is indicated, and the form it is to take, depends on the individual case and is subject to a medical assessment (diagnosis) which takes account of the signs, symptoms and/or dysfunctions present, the risks of developing certain signs, symptoms and/or dysfunctions, and other factors.

The treatment usually takes place by administration once or more than once a day, where appropriate together or alternately with other active ingredients or active ingredient-containing products, so that an individual to be treated is given a. daily dose preferably of about 0.1 to 1000 mg/kg of body weight on oral administration or of about 0.1 to 100 mg/kg of body weight on parenteral administration.

The invention also relates to the production of pharmaceutical compositions for the treatment of an individual, preferably a mammal, in particular a human or agricultural or domestic animal. Thus, the ligands are usually administered in the form of pharmaceutical compositions which comprise a pharmaceutically acceptable excipient with at least one ligand of the invention and, where appropriate, further active ingredients. These compositions can be administered for example by the oral, rectal, transdermal, subcutaneous, intravenous, intramuscular or intranasal route.

Examples of suitable pharmaceutical formulations are solid pharmaceutical forms such as oral powders, dusting powders, granules, tablets, especially film-coated tablets, pastilles, sachets, cachets, sugar-coated tablets, capsules such as hard and soft gelatine capsules, suppositories or vaginal pharmaceutical forms, semisolid pharmaceutical forms such as ointments, creams, hydrogels, pastes or patches, and liquid pharmaceutical forms such as solutions, emulsions, especially oil-in-water emulsions, suspensions, for example lotions, preparations for injection and infusion, eye drops and ear drops. Implanted delivery devices can also be used to administer inhibitors of the invention. A further possibility is also to use liposomes or microspheres.

The compositions are produced by mixing or diluting inhibitors of the invention usually with an excipient. Excipients may be solid, semisolid or liquid materials which serve as vehicle, carrier or medium for the active ingredient.

Suitable excipients are listed in the relevant pharmaceutical monographs. The formulations may additionally comprise pharmaceutically acceptable carriers or conventional excipients such as lubricants; wetting agents; emulsifying and suspending agents; preservatives; antioxidants; antiirritants; chelating agents; tablet-coating aids; emulsion stabilizers; film formers; gel formers; odor-masking agents; masking flavors; resins; hydrocolloids; solvents; solubilizers; neutralizers; permeation promoters; pigments; quaternary ammonium compounds; refatting and superfatting agents; ointment, cream or oil bases; silicone derivatives; spreading aids; stabilizers; sterilants; suppository bases; tablet excipients such as binders, fillers, lubricants, disintegrants or coatings; propellants; desiccants; opacifiers; thickeners; waxes; plasticizers; white oils. An arrangement concerning this is based on expert knowledge as set forth for example in Fiedler, H. P., Lexikon der Hilfsstoffe für Pharmacie, Kosmetik und angrenzende Gebiete, 4th edition, Aulendorf: ECV-Editio-Kantor-Verlag, 1996.

The following examples serve to illustrate the invention further but are not to be understood as restrictive.

A Preparation of the Compounds of the Invention of the Formula I

The nuclear magnetic resonance spectral properties (NMR) relate to chemical shifts ($\delta$) expressed in parts per million (ppm). The relative area for the shifts in the $^1$H-NMR spectrum corresponds to the number of hydrogen atoms for a particular functional type in the molecule. The nature of the shift in terms of the multiplicity is stated as singlet (s), broad singlet (s. br.), doublet (d), broad doublet (d br.), triplet (t), broad triplet (t br.), quartet (q), quintet (quint.), multiplet (m).

MS stands for Mass Specrum.

I. Preparation of the Substituted Benzazepines of the General formula II or IIa

Preparation Example 1: 3 Propyl-2,3,4,5-tetrahydro-1H-3-benzazepine 1.1 Methyl o-phenylenediacetate 26 g (133.9 mmol) of o-phenylenediacetic acid were dissolved in 217 ml of methanol under a nitrogen atmosphere: 25 ml (344 mmol) of thionyl chloride were added dropwise thereto at room temperature over the course of 45 minutes, during which the temperature occasionally rose to 50° C. After 1 hour, the reaction solution was mixed with 100 ml of saturated sodium bicarbonate solution and extracted with diethyl ether. The organic phase was dried with sodium sulfate, filtered and evaporated. Yield: 27.7 g (99% of theory)

$^1$H-NMR (500 MHz, CDCl$_3$): 7.2 (s, 4H); 3.7 (s, 4H); 3.6 (s, 6H).

1.2 1,2-Bis(2-Hydroxyethyl)Benzene 200 ml of tetrahydrofuran were added dropwise to 20 g (527 mmol) of lithiumaluminum hydride under a nitrogen atmosphere while cooling in ice. 27.7 g (133.6 mmol) of methyl o-phenylenediacetate were dissolved in 120 ml of tetrahydrofuran and added dropwise to the reaction solution over the course of 45 minutes, keeping the temperature at between 5 and 10° C. After a further 10 minutes, the reaction solution was mixed with 80 ml of a 1:1 mixture (v/v) of water and tetrahydrofuran while cooling in ice. The resulting viscous suspension was diluted with 100 ml of dichloromethane and adjusted to pH 4-6 with concentrated hydrochloric acid, and the precipitated solid was filtered off with suction. The filtrate was evaporated, dissolved in 400 ml of diethyl ether, dried with magnesium sulfate, filtrered and evaporated. Yield: 22.2 g (99% of theory)
$^1$H-NMR (500 MHz, CDCl$_3$): 7.2 (s, 4H); 3.9 (m, 4H); 3.0 (m, 4H); 2.4 (m, 2H).

1.3 1,2-Bis-(2-Methylsulfonyloxyethyl)Benzene 13.41 g (80.7 mmol) of 1,2-bis(2-hydroxyethyl)benzene and 33.7 ml (242 mmol) of triethylamine were dissolved in 300 ml of dichloromethane under a nitrogen atmosphere. While cooling in ice, 18 ml (231.5 mmol) of methanesulfonyl chloride were added dropwise over the course of 10 minutes. After a further 10 minutes, the reaction solution was extracted with 2×75 ml of water. The organic phase was dried with magnesium sulfate, filtered and evaporated. Yield: 25.9 g (99% of theory)
$^1$H-NMR (500 MHz, CDCl$_3$): 7.2 (s, 4H); 4.4 (m, 4H); 3.1 (m, 4H); 2.9 (s, 6H).

1.4 3-Propyl-2,3,4,5-Tetrahydro-1H-3-Benzazepine 22.6 g (70.1 mmol) of 1,2-bis(2-methylsulfonyloxyethyl)benzene were dissolved in 28.8 ml (350.5 mmol) of n-propylamine and stirred at room temperature for 48 hours. The reaction solution was mixed with 150 ml of diethyl ether and extracted with 2×35 ml of water. The organic phase was dried with magnesium sulfate, filtered and evaporated. Yield: 14.6 g (84% of theory)

Compounds II Nos. 2 to 6 indicated in Table 2 below were prepared in an analogous manner in preparation examples 2 to 6.

Preparation Example 7: 2,3,4,5-Tetrahydro-1H-3-benzazepine

Method A 11.55 g (48.66 mmol) of 3-benzyl-2,3,4,5-tetrahydro-1H-3-benzazepine were dissolved in 100 ml of ethanol, 300 ml of water and 8 ml of concentrated hydrochloric acid. Then 622 mg (0.59 mmol) of palladium on activated carbon (10%) were added, and the mixture was stirred under a hydrogen atmosphere at room temperature for 48 h. The catalyst was filtered off and washed with ethanol and water. The ethanol was evaporated off, and the aqueous phase was made alkaline with 50% strength sodium hydroxide solution and extracted 3× with 80 ml of diethyl ether each time. The aqueous phase was saturated with sodium chloride and again extracted 4× with 50 ml of diethyl ether each time. The combined organic phases were dried with magnesium sulfate, filtered and evaporated. Yield: 6.8 g (95% of theory)

Method B 32.66 g (89.15 mmol) of 1,2-bis(2-methylsulfonyloxyethyl)benzene were stirred in 320 ml of ethanol at 80° C. in a microwave for 10 minutes and cooled. Then 320 ml of 25% strength aqueous ammonium hydroxide solution were added, and the mixture was stirred at 80° C. in the microwave for 30 minutes. The solvent was evaporated for workup. The aqueous phase was acidified with hydrochloric acid and extracted twice with 100 ml of diethyl ether each time. The aqueous phase was made alkaline with 50% strength sodium hydroxide solution and extracted several times with dichloromethane. The combined organic phases were washed once with water, dried and evaporated. Yield: 10.25 g (73% of theory)

Preparation Example 8: 3-(Cyclohexylmethyl)2,3,4,5-Tetrahydro-1H-3-Benzazepine 2.16 g (10.2 mmol) of sodium acetoxyborohydride were added to 1 g (6.8 mmol) of 2,3,4,5-tetrahydro-1H-3-benzazepine and 0.84 ml (6.8 mmol) of cyclohexanecarbaldehyde, dissolved in 30 ml of dichloroethane, and 0.39 ml (6.8 mmol) of acetic acid, and the mixture was stirred at room temperature for 10 h. The reaction solution was mixed with dichloromethane and washed once each with 1 molar sodium hydroxide solution, water and saturated sodium chloride solution. The organic phase was dried with magnesium sulfate, filtered and evaporated.

Compounds II No. 9 Indicated in Table 2 Below Was Prepared in an Analogous Manner in Preparation Example 9.

TABLE 2

(II)

| Comp. II No. | R$^1$ | MS, $^1$H-NMR, m.p. |
|---|---|---|
| 1 | n-Propyl | MS [m + 1]: 190<br>$^1$H-NMR (360 MHz, CDCl$_3$): 7.1 (m, 4 H); 2.9 (m, 4 H); 2.7 (m, 4 H); 2.5 (m, 2 H); 1.5 (m, 2 H); 0.9 (m, 3 H). |
| 2 | Cyclopropyl | MS [m + 1]: 188<br>$^1$H-NMR (400 MHz, CDCl$_3$): 7.1 (m, 4 H); 2.9-2.8 (m, 8 H); 1.8 (m, 1 H); 0.5 (m, 6 H). |
| 3 | Cyclopentyl | MS [m + 1]: 216 |
| 4 | 1-Ethylpropyl | MS [m + 1]: 218 |
| 5 | Methyl | MS [m + 1]: 162 |
| 6 | Phenyl-CH$_2$— | MS [m + 1]: 238 |
| 7 | H | MS [m + 1]: 148 |
| 8 | Cyclohexyl-CH$_2$— | MS [m + 1]: 244 |
| 9 | CF$_3$—CH$_2$—CH$_2$— | MS [m + 1]: 244 |

II. Preparation of 7-Nitro-2,3,4,5-Benzazepines of the Formula III

Preparation Example 10: 7-Nitro-3-propyl-2,3,4,5-tetrahydro-1H-3-benzazepine 176 mg (1.74 mmol) of potassium nitrate were added in portions to 300 mg (1.49 mmol) of 3-propyl-2,3,4,5-tetrahydro-1H-3-benzazepine, dissolved in 2 ml of concentrated sulfuric acid, while cooling in ice, and the mixture was allowed to warm to room temperature over the course of 1 hour. The reaction solution was then mixed with ice, made alkaline with aqueous 50% strength sodium hydroxide solution and extracted twice with diethyl ether. The combined organic phases were dried with magnesium sulfate, filtered and evaporated. Yield: 310 mg (84% of theory)

Compounds III Nos. 2 to 6 indicated in Table 3 below were prepared in an analogous manner (Preparation examples 11-14).

TABLE 3

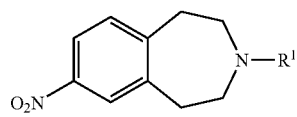

(III)

| Comp. III No. | R¹ | MS, ¹H-NMR, m.p. |
|---|---|---|
| 1 | n-Propyl | MS [m + 1]: 235 |
| 2 | Cyclopropyl | MS [m + 1]: 233 |
| 3 | Cyclopentyl | MS [m + 1]: 261 |
| 4 | 1-Ethylpropyl | MS [m + 1]: 263 |
| 5 | Cyclohexyl-$CH_2$— | MS [m + 1]: 289 |
| 6 | $CF_3$—$CH_2$—$CH_2$— | MS [m + 1]: 289 |

III. Preparation of 7-Amino-2,3,4,5-Benzazepines of the Formula III

Preparation example 16: 3-Propyl-2,3,4,5-Tetrahydro-1H-3-Benzazepine-7-Amine 5.7 g (24.33 mmol) of 7-nitro-3-propyl-2,3,4,5-tetrahydro-1H-3-benzazepine were dissolved in 100 ml of ethanol and 10 ml of water, mixed with 350 mg of palladium on activated carbon (10%) and then hydrogenated with hydrogen for 10 hours. The catalyst was filtered off, and the filtrate was evaporated. The residue was dissolved in 100 ml of diethyl ether, dried with magnesium sulfate, filtered and evaporated. Yield: 4.62 g (88% of theory)

Compounds IV Nos. 2 to 6 indicated in Table 4 below were prepared in an analogous manner (Preparation examples 16-20).

TABLE 3

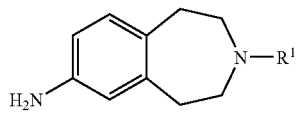

(IV)

| Comp. IV No. | R¹ | MS, ¹H-NMR, m.p. |
|---|---|---|
| 1 | n-Propyl | MS [m + 1]: 205<br>¹H-NMR (400 MHz, $CDCl_3$) of the hydrochloride:<br>11.0 (s, 1 H); 10.1 (bs, 1 H); 7.3 (d, 1 H); 7.2 (m, 2 H); 3.7 (m, 2 H); 3.5 (m, 2 H); 3.1-3.0 (m, 6 H); 1.8 (m, 2 H); 0.9 (t, 3 H). |
| 2 | Cyclopropyl | MS [m + 1]: 203 |
| 3 | Cyclopentyl | MS [m + 1]: 231 |
| 4 | 1-Ethylpropyl | MS [m + 1]: 233 |
| 5 | Cyclohexyl-$CH_2$— | MS [m + 1]: 259 |
| 6 | $CF_3$—$CH_2$—$CH_2$— | MS [m + 1]: 259 |

IV. Preparation of the Compounds of the Invention of General Formula I

EXAMPLE 1

N-(4-{[(3-Propyl-2,3,4,5-tetrahydro-1H-3-benzazepin-7-yl)amino]sulfonyl}-phenyl)acetamide 400 mg (1.96 mmol) of 3-propyl-2,3,4,5-tetrahydro-1H-3-benzazepine-7-amine and 1.86 mmol of 4-acetylaminobenzenesulfonyl chloride were dissolved in 20 ml of tetrahydrofuran at room temperature, 0.82 ml (5.87 mmol) of triethylamine was added dropwise, and the mixture was stirred at room temperature overnight. After the solvent had been evaporated off, 20 ml of water were added, and the mixture was acidified with 1 mol of hydrochloric acid and extracted with 50 ml of diethyl ether. The aqueous phase was made basic at pH 9-10 with 1 mol of sodium hydroxide solution and then extracted with diethyl ether. The residue obtained after drying with sodium sulfate and after removal of the solvent was converted into the hydrochloride with ethereal hydrochloric acid. Yield: 280 mg (35% of theory)

¹H-NMR (500 MHz, DMSO): 10.3 (s, 1H); 9.9 (bs, 1H); 7.7 (d, 2H); 7.6 (d, 2H); 6.9 (d, 1H); 6.8 (m, 2H); 2.7 (m, 4H), 2.5-2.4 (m, 4H); 2.3 (t, 2H); 2.1 (s, 3H); 1.5 (q, 2H); 0.8 (t, 3H).

MS [m+1]: 402

The following compounds I.A of Examples 2 to 30 were prepared in an analogous manner.

EXAMPLE 2

N-(3-Propyl-2,3,4,5-Tetrahydro-1H-3-Benzazepin-7-yl)-4-Trifluoromethoxy-Benzenesulfonamide ¹H-NMR (500 MHz, DMSO): 10.2 (bs, 1H); 7.8 (d, 2H); 7.6 (d, 2H); 7.0 (d, 1H); 6.8 (m, 2H); 2.7 (m, 4H); 2.5-2.4 (m, 4H); 2.3 (t, 2H); 1.4 (q, 2H); 0.8 (t, 3H).

MS [m+1]: 429

EXAMPLE 3

4-Chloro-N-(3-Propyl-2,3,4,5-Tetrahydro-1H-3-Benzazepin-7-yl)Benzenesulfonamide ¹H-NMR (500 MHz, DMSO): 10.4 (bs, 1H); 7.7 (d, 2H); 7.6 (d, 2H); 7.0 (d, 1H); 6.8 (m, 2H); 3.2 (m, 2H); 2.7 (m, 4H); 2.5-2.4 (m, 4H); 1.5 (m, 2H); 0.8 (t, 3H).
MS [m+1]: 379

EXAMPLE 4

N-(3-Propyl-2,3,4,5-Tetrahydro-1H-3-Benzazepin-7-yl)-4-Vinylbenzenesulfonamide Hydrochloride ¹H-NMR (500 MHz, DMSO): 10.5 (bs, 1H); 10.3 (s, 1H); 7.7 (d, 2H); 7.6 (d, 2H); 7.1 (d, 1H); 7.0 (s, 1H); 6.9 (d, 1H); 6.8 (dd, 1H); 6.0 (d, 1H); 5.4 (d, 1H); 3.6 (m, 2H); 3.3 (m, 2H); 3.0 (m, 2H); 2.9 (m, 4H); 1.7 (m, 2H); 0.9 (t, 3H).
MS [m+1]: 371

EXAMPLE 5

4-Ethyl-N-(3-Propyl-2,3,4,5-Tetrahydro-1H-3-Benzazepin-7-yl)Benzenesulfonamide Hydrochloride MS [m+1]: 373

EXAMPLE 6

N-(3-Propyl-2,3,4,5-Tetrahydro-1H-3-Benzazepin-7-yl)-4-(Trifluoromethyl)-Benzenesulfonamide Hydrochloride ¹H-NMR (500 MHz, DMSO): 10.6 (s, 1H); 8.0 (s, 4H); 7.1 (d, 1H); 7.0 (s, 1H); 6.9 (d, 1H); 3.6 (m, 2H); 3.3 (m, 2H); 3.0 (m, 2H); 2.9 (m, 4H); 1.7 (m, 2H); 0.9 (t, 3H).
MS [m+1]: 413

EXAMPLE 7

4-Tert-Butyl-N-(3-Propyl-2,3,4,5-Tetrahydro-1H-3-Benzazepin-7-yl)Benzenesulfonamide Hydrochloride ¹H-NMR (500 MHz, DMSO): 10.7 (bs, 1H); 10.3 (s, 1H); 7.7 (d, 2H); 7.6 (d, 2H); 7.1 (d, 1H); 7.0 (m, 2H); 3.6 (m, 2H); 3.3 (m, 2H); 3.0 (m, 2H); 2.9 (m, 4H); 1.7 (m, 2H); 1.3 (s, 9H); 0.9 (t, 3H).
MS [m+1]: 401

EXAMPLE 8

4-Isopropyl-N-(3-Propyl-2,3,4,5-Tetrahydro-1H-3-Benzazepin-7-yl)Benzenesulfonamide Hydrochloride ¹H-NMR (500 MHz, CDCl₃): 12.4 (bs, 1H); 7.7 (d, 2H); 7.5 (s, 1H); 7.3 (m, 3H); 7.0 (m, 2H); 3.8 (m, 2H); 3.0 (m, 1H); 2.8 (m, 2H); 1.9 (m, 2H); 1.6 (m, 4H); 1.3 (d, 6H); 1.0 (t, 3H).
MS [m+1]: 387

EXAMPLE 9

N-(3-Propyl-2,3,4,5-Tetrahydro-1H-3-Benzazepin-7-yl)Benzenesulfonamide Hydrochloride ¹H-NMR (500 MHz, DMSO): 10.8 (bs, 1H); 10.3 (s, 1H); 7.8 (d, 2H); 7.6 (m, 1H); 7.5 (m, 2H); 7.1 (d, 1H); 6.9 (s, 1H); 6.8 (d, 1H); 3.6 (m, 2H); 3.3 (m, 2H); 3.0 (m, 2H); 2.8 (m, 2H); 1.7 (m, 2H); 0.9 (t, 3H).

EXAMPLE 10

4-Acetyl-N-(3-Propyl-2,3,4,5-Tetrahydro-1H-3-Benzazepin-7-yl)Benzenesulfonamide ¹H-NMR (500 MHz, CDCl₃): 8.0 (d, 2H); 7.8 (d, 2H); 6.9 (d, 1H); 6.8 (s, 1H); 6.7 (d, 1H); 2.8 (m, 4H); 2.7 (s, 3H); 2.6 (m, 4H); 2.4 (m, 2H); 1.5 (m, 2H); 0.9 (t, 3H).
MS [m+1]: 387

EXAMPLE 11

4-Methyl-N-(3-Propyl-2,3,4,5-Tetrahydro-1H-3-Benzazepin-7-yl)Benzene Sulfonamide Trifluoroacetate MS [m+1]: 359

EXAMPLE 12

2,4,6-Trimethyl-N-(3-Propyl-2,3,4,5-Tetrahydro-1H-3-Benzazepin-7-yl)-Benzenesulfonamide Trifluoroacetate MS [m+1]: 387

EXAMPLE 13

4-Butyl-N-(3-Propyl-2,3,4,5-Tetrahydro-1H-3-Benzazepin-7-yl)Benzene-Sulfonamide Trifluoroacetate MS [m+1]: 401

EXAMPLE 14

4-(1,1-Dimethylpropyl)-N-(3-Propyl-2,3,4,5-Tetrahydro-1H-3-Benzazepin-7-yl)Benzenesulfonamide Trifluoroacetate MS [m+1]: 415

EXAMPLE 15

3-Chloro-4-Methyl-N-(3-Propyl-2,3,4,5-Tetrahydro-1H-3-Benzazepin-7-yl)-Benzenesulfonamide Trifluoroacetate MS [m+1]: 393

EXAMPLE 16

4-Methoxy-N-(3-Propyl-2,3,4,5-Tetrahydro-1H-3-Benzazepin-7-yl)Benzene-Sulfonamide Trifluoroacetate MS [m+1]: 375

EXAMPLE 17

N-(3-Propyl-2,3,4,5-Tetrahydro-1H-3-Benzazepin-7-yl)Naphthalene-2-Sulfonamide Trifluoroacetate MS [m+1]: 395

EXAMPLE 18

2,4-Dichloro-N-(3-Propyl-2,3,4,5-Tetrahydro-1H-3-Benzazepin-7-yl)Benzenesulfonamide Trifluoroacetate MS [m+1]: 414

EXAMPLE 19

4-Bromo-N-(3-Propyl-2,3,4,5-Tetrahydro-1H-3-Benzazepin-7-yl)Benzene-Sulfonamide Trifluoroacetate MS [m+1]: 423

EXAMPLE 20

4-Bromo-2-Methyl-N-(3-Propyl-2,3,4,5-Tetrahydro-1H-3-Benzazepin-7-yl)-Benzenesulfonamide Trifluoroacetate MS [m+1]: 437

EXAMPLE 21

N-(3-Propyl-2,3,4,5-Tetrahydro-1H-3-Benzazepin-7-yl)-5-Chlorothiophene-2-Sulfonamide Trifluoroacetate MS [m+1]: 385

EXAMPLE 22

N-(3-Propyl-2,3,4,5-Tetrahydro-1H-3-Benzazepin-7-yl)-2,5-Dichlorothiophene-3-Sulfonamide Trifluoroacetate MS [m+1]: 419

EXAMPLE 23

N-(3-Cyclopropyl-2,3,4,5-Tetrahydro-1H-3-Benzazepin-7-yl)-4-(Trifluoromethoxy) Benzenesulfonamide Hydrochloride $^1$H-NMR (500 MHz, CDCl$_3$): 11.8 (bs, 1H); 8.2 (s, 1H); 7.9 (d, 2H); 7.3 (d, 2H); 6.9 (m, 2H); 3.8 (m, 2H); 3.7 (m, 2H); 2.8 (m, 2H); 2.7 (m, 2H); 2.5 (m, 1H); 1.8 (m, 2H); 1.7 (m, 2H).
MS [m+1]: 427

EXAMPLE 24

N-(3-Cyclopentyl-2,3,4,5-Tetrahydro-1H-3-Benzazepin-7-yl)-4-(Trifluoromethoxy)Benzenesulfonamide H-NMR (500 MHz, CDCl$_3$): 7.8 (d, 2H); 7.3 (m, 2H); 7.0 (d, 1H); 6.8 (m, 2H); 2.8 (m, 5H); 2.6 (m, 4H); 1.9 (m, 2H); 1.7 (m, 2H); 1.5 (m, 2H); 1.4 (m, 2H).
MS [m+1]: 455

EXAMPLE 25

N-[3-(Cyclohexylmethyl)-2,3,4,5-Tetrahydro-1H-3-Benzazepin-7-yl]-4-(Trifluoromethoxy)Benzenesulfonamide Hydrochloride $^1$H-NMR (500 MHz, DMSO): 10.5 (s, 1H); 9.9 (bs, 1H); 7.9 (d, 2H); 7.6 (d, 2H); 7.1 (d, 1H); 7.0 (s, 1H); 6.9 (d, 1H); 3.6 (m, 2H); 3.3 (m, 6H); 2.9 (m, 2H); 1.7 (m, 6H); 1.3 (m, 2H); 1.2 (m, 1H); 1.0 (m, 2H).
MS [m+1]: 483

EXAMPLE 26

N-[3-(Cyclohexylmethyl)-2,3,4,5-Tetrahydro-1H-3-Benzazepin-7-yl]-4-(Trifluoromethyl)Benzenesulfonamide $^1$H-NMR (500 MHz, CDCl$_3$): 7.9 (d, 2H); 7.7 (d, 2H); 7.0 (d, 1H); 6.8 (m, 2H); 2.8 (m, 4H); 2.5 (m, 4H); 2.2 (m, 2H); 1.8 (m, 6H); 1.5 (m, 1H); 1.3 (m, 2H); 0.9 (m, 2H).
MS [m+1]: 467

EXAMPLE 27

N-[3-(1-Ethylpropyl)-2,3,4,5-Tetrahydro-1H-3-Benzazepin-7-yl]-4-(Trifluoromethoxy)Benzenesulfonamide Hydrochloride $^1$H-NMR (500 MHz, DMSO): 10.5 (s, 1H); 10.1 (bs, 1H); 7.9 (d, 2H); 7.5 (d, 2H); 7.1 (d, 1H); 6.9 (m, 2H); 3.5 (m, 2H); 3.4 (m, 2H); 3.2 (m, 1H); 3.0 (m, 2H); 2.8 (m, 2H); 1.9 (m, 2H); 1.5 (m, 2H); 1.0 (m, 6H).
MS [m+1]: 457

EXAMPLE 28

N-[3-(1-Ethylpropyl)-2,3,4,5-Tetrahydro-1H-3-Benzazepin-7-yl]-4-(Trifluoromethyl)Benzenesulfonamide Hydrochloride $^1$H-NMR (500 MHz, DMSO): 10.5 (s, 1H); 10.2 (bs, 1H); 8.0 (s, 4H); 7.1 (d, 1H); 7.0 (s, 1H); 6.9 (d, 2H); 3.5 (m, 4H); 3.1 (m, 1H); 3.0 (m, 2H); 2.9 (m, 2H); 1.9 (m, 2H); 1.5 (m, 2H); 1.0 (m, 6H).
MS [m+1]: 441

EXAMPLE 29

4-(Trifluoromethoxy)-N-[3-(3,3,3-Trifluoropropyl)-2,3,4,5-Tetrahydro-1H-3-benzazepin-7-yl]Benzenesulfonamide Hydrochloride $^1$H-NMR (500 MHz, DMSO): 13.0 (s, 1H); 8.1 (s, 1H); 7.9 (d, 2H); 7.3 (d, 2H); 7.0 (m, 3H); 3.8 (m, 4H); 3.3 (m, 2H); 3.0 (m, 2H); 2.8 (m, 4H).
MS [m+1]: 483

EXAMPLE 30

4-(Trifluoromethyl)-N-[3-(3,3,3-Trifluoropropyl)-2,3,4,5-Tetrahydro-1H-3-Benzazepin-7-yl]Benzenesulfonamide ¹H-NMR (500 MHz, DMSO): 7.9 (d, 2H); 7.7 (d, 2H); 7.0 (d, 1H); 6.9 (s, 1H); 6.8 (d, 1H); 6.6 (bs, 1H); 2.8 (m, 4H); 2.7 (m, 2H); 2.6 (m, 4H); 2.3 (m, 2H).
MS [m+1]: 467

EXAMPLE 31

4-Isopropyl-N-Methyl-N-(3-Propyl-2,3,4,5-tetrahydro-1H-3-Benzazepin-7-yl)Benzenesulfonamide Trifluoroacetate 21.5 mg (0.45 mmol) of sodium hydride were introduced under a nitrogen atmosphere into 4 ml of tetrahydrofuran, 144 mg (0.37 mmol) of 4-isopropyl-N-(3-propyl-2,3,4,5-tetrahydro-1H-3-benzazepin-7-yl)benzenesulfonamide were added, and the mixture was stirred at room temperature for 15 minutes. Then 23 µl (0.37 mmol) of methyl iodide were added, and the mixture was stirred overnight. The solvent was evaporated off, the residue was taken up in water, and the aqueous phase was adjusted to a pH of pH 10-11. This was followed by extraction with diethyl ether several times, drying with magnesium sulfate, filtration and evaporation. The residue was purified by HPLC and then lyophilized. Yield: 13 mg (7% of theory)
¹H-NMR (400 MHz, CDCl₃): 12.8 (bs, 1H); 7.5 (d, 2H); 7.3 (d, 2H); 7.1 (d, 1H); 7.0 (s, 1H); 6.9 (d, 1H); 3.8 (m, 2H); 3.6 (m, 2H); 3.2 (s, 3H); 3.1-2.8 (m, 5H); 2.4 (m, 2H); 1.3 (d, 6H); 1.1 (t, 3H).
MS [m+1]: 401
The compound in Example 32 was prepared in an analogous manner.

EXAMPLE 32

N-Methyl-N-(3-Propyl-2,3,4,5-Tetrahydro-1H-3-Benzazepin-7-yl)-4-Trifluoro-Methoxybenzenesulfonamide MS [m+1]: 443

EXAMPLE 33

N-Phenyl-3-Propyl-2,3,4,5-Tetrahydro-1H-3-Benzazepine-7-Sulfonamide Hydrochloride 33.1 3-Propyl-2,3,4,5-tetrahydro-1H-3-benzazepine-7-sulfonyl chloride
4.3 ml (64.57 mmol) of chlorosulfonic acid were introduced into a flask under a nitrogen atmosphere and, at a temperature of 5-15° C., 2.7 g (12.84 mmol) of 3-propyl-2,3,4,5-tetrahydro-1H-3-benzazepine were added and stirred while cooling in ice for 1 hour. The reaction solution was then added to 75 g of ice and extracted with 2×50 ml of dichloromethane. The organic phase was washed with saturated sodium chloride solution, dried with magnesium sulfate, filtered and evaporated. Yield: 1.25 g (31% of theory)
MS [m+1]: 288
33.2 N-Phenyl-3-propyl-2,3,4,5-tetrahydro-1H-3-benzazepine-7-sulfonamide hydrochloride
250 mg (0.79 mmol) of 3-propyl-2,3,4,5-tetrahydro-1H-3-benzazepine-7-sulfonyl chloride and 0.79 mmol of aniline were dissolved in 10 ml of tetrahydrofuran and stirred with 0.41 ml (2.40 mmol) of diisopropylethylamine at room temperature for 5 minutes. The tetrahydrofuran was evaporated off, and the residue was mixed with 5 ml of water and extracted with 20 ml of ethyl acetate. The residue obtained after drying with sodium sulfate and after removal of the solvent was converted into the hydrochloride with ethereal hydrochloric acid.
Yield: 56 mg (17% of theory)
¹H-NMR (500 MHz, DMSO): 10.6 (bs, 1H); 10.4 (s, 1H); 7.7 (m, 1H); 7.6 (d, 1H); 7.4 (d, 1H); 7.2 (m, 2H); 7.1 (m, 2H); 7.0 (m, 1H); 3.7 (m, 2H); 3.4 (m, 4H); 3.1 (m, 4H); 1.7 (m, 2H); 0.9 (t, 3H).
MS [m+1]: 345
The compounds of Examples 34 and 35 were prepared in an analogous manner.

EXAMPLE 34

N-Methyl-N-Phenyl-3-Propyl-2,3,4,5-Tetrahydro-1H-3-Benzazepine-7-Sulfonamide Hydrochloride ¹H-NMR (500 MHz, DMSO): 10.8 (bs, 1H); 7.5 (m, 2H); 7.4 (m, 2H); 7.3 (m, 2H); 7.1 m, 2H); 3.7 (m, 2H); 3.5 (m, 4H); 3.2 (s, 3H); 3.1 (m, 2H); 3.0 (m, 2H); 1.8 (m, 2H); 0.9 (t, 3H).
MS [m+1]: 359

EXAMPLE 35

3-Propyl-N-[4-(Trifluoromethoxy)Phenyl]-2,3,4,5-Tetrahydro-1H-3-Benzazepine-7-Sulfonamide Hydrochloride ¹H-NMR (500 MHz, DMSO): 10.6 (bs, 1H); 7.7 (m, 1H); 7.6 (d, 1H); 7.4 (d, 1H); 7.3 (d, 2H); 7.2 (d, 2H); 3.7 (m, 2H); 3.2-3.0 (m, 8H); 1.7 (m, 2H); 0.9 (t, 3H).
MS [m+1]: 429

EXAMPLE 36

7-(4-Isopropylbenzenesulfonylmethyl)-3-Propyl-2,3,4,5-Tetrahydro-1H-3-Benzazepine 36.1 Methyl 3-propyl-2,3,4,5-tetrahydro-1H-3-benzazepine-7-carboxylate
2.99 g (22.43 mmol) of aluminum trichloride were added to 1.9 g (7.48 mmol) of 3-propyl-2,3,4,5-tetrahydro-1H-3-benzazepine and 1.29 ml (14.95 mmol) of oxalyl chloride in 40 ml of dichloromethane under a nitrogen atmosphere at 0-5° C. and then stirred at room temperature overnight. 2 ml of methanol were added, and stirring was continued for 30 minutes. The reaction solution was concentrated and the residue was mixed with 25 ml of water and extracted with 25 ml of diethyl ether. The aqueous phase was then saturated with sodium chloride and extracted twice with ethyl acetate. The combined organic phases were dried with magnesium sulfate, filtered and evaporated. Yield: 720 mg (36% of theory)
MS [m+1]: 248
36.2 (3-Propyl-2,3,4,5-tetrahydro-1H-3-benzazepin-7-yl)methanol
720 mg (2.67 mmol) of methyl 3-propyl-2,3,4,5-tetrahydro-1H-3-benzazepine-7-carboxylate were dissolved in 10 ml of tetrahydrofuran under a nitrogen atmosphere and, at 0-5° C., 202 mg (5.34 mmol) of lithium aluminum hydride were added in portions. After stirring for 1 hour, the reaction mixture was worked up and then employed in the following reaction.

MS [m+1]: 220

36.3 7-Chloromethyl-3-propyl-2,3,4,5-tetrahydro-1H-3-benzazepine 180 mg (0.82 mmol) of (3-propyl-2,3,4,5-tetrahydro-1H-3-benzazepin-7-yl)methanol were dissolved in 25 ml of dichloromethane under a nitrogen atmosphere, and 0.34 ml (2.46 mmol) of triethylamine was added. Then 0.19 ml (2.46 mmol) of methanesulfonyl chloride was added, and the mixture was stirred at room temperature for 30 minutes. The reaction mixture was extracted twice with 10 ml of aqueous sodium bicarbonate solution. The organic phase was dried over magnesium sulfate, filtered and evaporated. Yield: 175 mg (77% of theory)

MS [m+1]: 238

36.4 7-(4-Isopropylphenylsulfanylmethyl)-3-propyl-2,3,4,5-tetrahydro-1H-3-benzazepine 175 mg (0.64 mmol) of 7-chloromethyl-3-propyl-2,3,4,5-tetrahydro-1H-3-benzazepine and 116 mg (0.76 mmol) of (4-isopropyl)thiophenol were dissolved in 5 ml of dimethylformamide under a nitrogen atmosphere, 189 mg (1.52 mmol) of potassium carbonate were added, and the mixture was stirred at 50° C. for 1 hour. Then 30 ml of water were added, and the mixture was acidified with dilute aqueous hydrochloric acid and extracted twice with 25 ml of diethyl ether each time. The combined organic phases were dried over magnesium sulfate, filtered, evaporated and stirred with 30 ml of diethyl ether. The crystals which separated out were filtered off with suction. Yield: 32 mg (11% of theory)

MS [m+1]: 354

36.5 7-(4-Isopropylbenzenesulfonylmethyl)-3-propyl-2,3,4,5-tetrahydro-1H-3-benzazepine hydrochloride 32 mg (0.07 mmol) of 7-(4-isopropylphenylsulfanylmethyl)-3-propyl-2,3,4,5-tetrahydro-1H-3-benzazepine were dissolved in 1 ml of methanol while cooling in ice. 66.5 mg (0.11 mmol) of oxone were dissolved in 1 ml of water and added dropwise to the reaction solution at the same time as a 1 N sodium hydroxide solution so that the pH was kept at 2-3. The reaction solution was then stirred at room temperature overnight. The reaction solution was then made alkaline (pH ~10) and extracted twice with 25 ml of diethyl ether each time. The combined organic phases were then extracted with 20 ml of water, and the organic phase was dried over magnesium sulfate, filtered and evaporated to dryness. The residue was dissolved in 10 ml of diethyl ether and mixed with ethereal hydrochloride solution. The precipitated solid was filtered off with suction and dried. Yield: 16 mg (48% of theory)

$^1$H-NMR (500 MHz, CDCl$_3$): 12.8 (bs, 1H); 7.7 (d, 2H); 7.4 (d, 2H); 7.2 (d, 1H); 7.1 (d, 1H); 7.0 (s, 1H); 4.2 (s, 2H); 3.9 (m, 2H); 3.7 (m, 2H); 3.0 (m, 1H); 2.9-2.8 (m, 6H); 1.9 (m, 2H); 1.3 (d, 6H); 1.0 (t, 3H).

MS [m+1]: 386

EXAMPLE 37

N-[3-(Trifluoroacetyl)-2,3,4,5-Tetrahydro-1H-3-Benzazepin-7-yl]4-(Trifluoromethyl)Benzenesulfonamide 37.1 3-(Trifluoroacetyl)-2,3,4,5-tetrahydro-1H-3-benzazepine 9.42 ml (67.74 mmol) of trifluoroacetic anhydride were mixed with 60 ml of dichloromethane under a nitrogen atmosphere at −20° C. 6.77 g (45.16 mmol) of 2,3,4,5-tetrahydro-1H-3-benzazepine were dissolved in 40 ml of dichloromethane and slowly added dropwise at a constant temperature of −20° C. The mixture was allowed to warm to room temperature over the course of 12 hours. Then 100 ml of ice-water were added and the reaction mixture was extracted twice with dichloromethane. The combined organic phases were dried with magnesium sulfate, filtered and evaporated.

Yield: 10.82 g (98% of theory)

MS [m+1]: 244

37.2 7-Nitro-3-(trifluoroacetyl)-2,3,4,5-tetrahydro-1H-3-benzazepine 4.262 g (42.15 mmol) of potassium nitrate were added in portions to 9.32 g (38.32 mmol) of 3-(trifluoroacetyl)-2,3,4,5-tetrahydro-1H-3-benzazepine, dissolved in 40 ml of concentrated sulfuric acid, while cooling in ice, and the mixture was stirred at room temperature for 10 hours. The reaction solution was then mixed with ice and extracted 2× each with diethyl ether and ethyl acetate.

The combined organic phases were dried with magnesium sulfate, filtered and evaporated.

Yield: 11.99 g (99% of theory)

MS [m+1]: 289

37.3 3-(Trifluoroacetyl)-2,3,4,5-tetrahydro-1H-3-benzazepine-7-amine 11.99 g (37.94 mmol) of 7-nitro-3-(trifluoroacetyl)-2,3,4,5-tetrahydro-1H-3-benzazepine were dissolved in a solvent mixture composed of 150 ml each of ethanol and ethyl acetate, 885 mg (0.83 mmol) of palladium on activated carbon (10%) were added, and the mixture was stirred at room temperature under a hydrogen atmosphere for 10 hours. The catalyst was then filtered off and the filtrate was evaporated. Yield: 10.53 g (76% of theory)

MS [m+1]: 259

37.4 N-[3-(Trifluoroacetyl)-2,3,4,5-tetrahydro-1H-3-benzazepin-7-yl]-4-(trifluoromethyl)benzenesulfonamide 1 g (2.68 mmol) of 3-(trifluoroacetyl)-2,3,4,5-tetrahydro-1H-3-benzazepine-7-amine and 947 mg (3.87 mmol) of 4-(trifluoromethyl)benzenesulfonyl chloride were dissolved in 20 ml of tetrahydrofuran at room temperature, and 1.62 ml (11.62 mmol) of triethylamine were added dropwise to the solution, which was stirred at room temperature overnight. After evaporation of the solvent, 20 ml of water were added and acidified with 1 mol of hydrochloric acid, and the aqueous phase was extracted with 50 ml of diethyl ether. The residue obtained after drying with sodium sulfate and after removal of the solvent was separated by column chromatography (cyclohexane/ethyl acetate 6:1).

Yield: 590 mg (46% of theory)

MS [m+1]: 467

The compounds of Examples 38 and 39 were prepared in an analogous manner:

EXAMPLE 38

N-[3-(Trifluoroacetyl)-2,3,4,5-tetrahydro-1H-3-Benzazepin-7-yl]-4-(Trifluoromethoxy)Benzenesulfonamide MS [m+1]: 483

EXAMPLE 39

4-Isopropyl-N-[3-(Trifluoroacetyl)-2,3,4,5-Tetrahydro-1H-3-Benzazepin-7-yl]Benzenesulfonamide $^1$H-NMR (400 MHz, CDCl$_3$): 7.7 (d, 2H); 7.3 (d, 2H); 7.0 (m, 1H); 6.8 (m, 1H); 6.6 (s, 1H); 3.7 (m, 2H); 3.6 (m, 2H); 2.9 (m, 5H); 1.2 (d, 6H).
MS [m+1]: 441

EXAMPLE 40

N-(2,3,4,5-Tetrahydro-1H-3-Benzazepin-7-yl)-4-(Trifluoromethyl)Benzene-Sulfonamide 2 g (3.84 mmol) of N-[3-(trifluoroacetyl)-2,3,4,5-tetrahydro-1H-3-benzazepin-7-yl]-4-trifluoromethyl)benzenesulfonamide from Example 37 were dissolved in 20 ml of methanol, 1.666 g (12.05 mmol) of potassium carbonate were added, and the mixture was stirred at room temperature for 10 hours. The solvent was then evaporated off, the residue was mixed with 75 ml of water, and the aqueous phase was extracted with diethyl ether. The combined organic phases were dried with magnesium sulfate, filtered and evaporated. Yield: 1.43 g (92% of theory)
$^1$H-NMR (500 MHz, CDCL$_3$): 7.9 (d, 2H); 7.7 (d, 2H); 7.0 (m, 1H); 6.9 (m, 2H); 3.7 (bs, 2H); 2.9 (m, 4H); 2.8 (m, 4H).
MS [m+1]: 371

The compounds of Examples 41 and 42 were prepared in an analogous manner.

EXAMPLE 41

N-(2,3,4,5-Tetrahydro-1H-3-Benzazepin-7-yl)-4-(Trifluoromethoxy)-Benzenesulfonamide $^1$H-NMR (500 MHz, CDCL$_3$): 7.8 (d, 2H); 7.3 (d, 2H); 7.0 (d, 1H); 6.8 (m, 2H); 3.3 (bs, 2H); 3.0 (m, 4H); 2.9 (m, 2H); 2.8 (m, 2H).
MS [m+1]: 387

EXAMPLE 42

4-Isopropyl-N-(2,3,4,5-Tetrahydro-1H-3-Benzazepin-7-yl)Benzenesulfonamide $^1$H-NMR (500 MHz, DMSO): 7.7 (d, 2H); 7.4 (d, 2H); 6.9 (d, 1H); 6.8 (m, 2H); 3.0 (m, 1H); 2.7 (bs, 8H); 1.2 (d, 6H).
MS [m+1]: 345

EXAMPLE 43

N-[3-(2-Methylbutyl)-2,3,4,5-Tetrahydro-1H-3-Benzazepin-7-yl]-4-(Trifluoromethyl)Benzenesulfonamide Hydrochloride Method A
48.5 mg (0.54 mmol) of 2-methylbutylraldehyde were dissolved in 10 ml of dichloromethane, and 30 µl (0.54 mmol) of glacial acetic acid, 200 mg (0.54 mmol) of N-(2,3,4,5-tetrahydro-1H-3-benzazepin-7-yl)-4-(trifluoromethyl)benzenesulfonamide and 172 mg (0.81 mmol) of sodium trisacetoxyborohydride were successively added, and the resulting mixture was stirred at room temperature for 30 minutes. The solvent was evaporated off, and the residue was taken up in water and extracted with diethyl ether. The residue obtained after drying with sodium sulfate and after removal of the solvent was converted into the hydrochloride with ethereal hydrochloric acid. Yield: 340 mg (62% of theory)
$^1$H-NMR (500 MHz, DMSO): 10.6 (s, 1H); 10.0 (bs, 1H); 8.0 (s, 4H); 7.1 (d, 1H); 7.0 (s, 1H); 6.9 (d, 1H); 3.6 (m, 2H); 3.4 (m, 2H); 3.0 (m, 1H); 3.0 (m, 5H); 1.9 (m, 1H); 1.5 (m, 1H); 1.2 (m, 1H); 1.0 (d, 3H); 0.9 (t, 3H).
MS [m+1]: 441

The compounds of Examples 44 to 57 were prepared in an analogous manner to Example 43.

EXAMPLE 44

N-[3-(4,4,4-Trifluorobutyl)-2,3,4,5-Tetrahydro-1H-3-Benzazepin-7-yl]-4-(Trifluoromethyl)Benzenesulfonamide $^1$H-NMR (500 MHz, CDCl$_3$): 7.9 (d, 2H); 7.7 (d, 2H); 7.0 (d, 1H); 6.9 (s, 1H); 6.8 (s, 1H); 6.6 (bs, 1H); 2.8 (m, 4H); 2.6 (m, 4H); 2.5 (m, 2H); 2.2 (m, 2H); 1.8 (m, 2H).
MS [m+1]: 481

EXAMPLE 45

N-[3-(4,4,4-Trifluorobutyl)-2,3,4,5-Tetrahydro-1H-3-benzazepin-7-yl]-4-(Trifluoromethoxy)Benzenesulfonamide Hydrochloride $^1$H-NMR (500 MHz, CDCl$_3$): 12.8 (s, 1H); 9.8 (s, 1H); 7.8 (d, 2H); 7.2 (d, 2H); 7.0 (m, 3H); 3.8 (m, 2H); 3.7 (m, 2H); 3.1 (m, 2H); 2.8 (m, 4H); 2.2 (m, 4H).
MS [m+1]: 497

EXAMPLE 46

N-[3-Isobutyl-2,3,4,5-Tetrahydro-1H-3-Benzazepin-7-yl]4-(Trifluoromethyl)-benzenesulfonamide hydrochloride $^1$H-NMR (500 MHz, CDCl$_3$): 10.6 (s, 1H); 9.9 (bs, 1H); 8.0 (s, 4H); 7.1 (d, 1H); 7.0 (s, 1H); 6.9 (d, 1H); 3.6 (m, 2H); 3.3 (m, 2H); 2.9 (m, 6H); 2.1 (m, 1H); 1.6 (d, 6H).
MS [m+1]: 427

EXAMPLE 47

N-[3-(Cyclopropylmethyl)-2,3,4,5-Tetrahydro-1H-3-benzazepin-7-yl]-4-(Trifluoromethyl)Benzenesulfonamide Hydrochloride $^1$H-NMR (500 MHz, CDCl$_3$): 10.6 (s, 1H); 10.5 (bs, 1H); 8.0 (s, 4H); 7.1 (d, 1H); 7.0 (s, 1H); 6.9 (d, 1H); 3.7 (m, 2H); 3.3 (m, 2H); 3.0 (m, 2H); 2.9 (m, 4H); 1.1 (m, 1H); 0.7 (m, 2H); 0.4 (m, 2H).
MS [m+1]: 425

EXAMPLE 48

N-(3-Ethyl-2,3,4,5-Tetrahydro-1H-3-Benzazepin-7-yl)-4-(Trifluoromethyl)-Benzenesulfonamide Hydrochloride $^1$H-NMR (500 MHz, DMSO): 10.6 (s, 1H); 10.5 (bs, 1H); 8.0 (s, 4H); 7.1 (d, 1H); 7.0 (s, 1H); 6.9 (d, 1H); 3.6 (m, 2H); 3.3 (m, 2H); 3.2 (m, 2H); 2.8 (m, 4H); 1.3 (t, 3H).
MS [m+1]: 399

EXAMPLE 49

N-{3-[3-(Cyclohexyloxy)Propyl]-2,3,4,5-Tetrahydro-1H-3-Benzazepin-7-yl}-4-(Trifluoromethyl)Benzenesulfonamide Hydrochloride $^1$H-NMR (500 MHz, DMSO): 10.6 (s, 1H); 10.2 (bs, 1H); 8.0 (s, 4H); 7.1 (d, 1H); 7.0 (s, 1H); 6.9 (d, 1H); 3.6 (m, 2H); 3.5 (m, 2H); 3.2 (m, 4H); 2.9 (m, 4H); 1.9 (m, 2H); 1.8 (m, 2H); 1.7 (m, 2H); 1.5 (m, 1H); 1.2 (m, 6H).
MS [m+1]: 511

EXAMPLE 50

N-{3-[3-(cyclohexyloxy)propyl]-2,3,4,5-Tetrahydro-1H-3-Benzazepin-7-yl}-4-Isopropylbenzenesulfonamide Hydrochloride $^1$H-NMR (500 MHz, DMSO): 10.6 (bs, 1H); 10.3 (s, 1H); 7.7 (d, 2H); 7.4 (d, 2H); 7.1 (d, 1H); 6.9 (m, 2H); 3.6 (m, 2H); 3.4 (m, 2H); 3.3 (m, 2H); 3.1 (m, 2H); 2.9 (m, 5H); 1.9 (m, 2H); 1.8 (m, 2H); 1.7 (m, 2H); 1.5 (m, 1H); 1.2 (m, 12H).
MS [m+1]: 485

EXAMPLE 51

N-[3-(2-Methoxyethyl)-2,3,4,5-Tetrahydro-1H-3-Benzazepin-7-yl]4-(Trifluoromethyl)Benzenesulfonamide Hydrochloride $^1$H-NMR (500 MHz, DMSO): 10.6 (s, 1H); 10.5 (bs, 1H); 8.0 (s, 4H); 7.1 (d, 1H); 7.0 (s, 1H); 6.9 (d, 1H); 3.7 (m, 2H); 3.6 (m, 2H); 3.4 (m, 2H); 3.3 (s, 3H); 3.2 (m, 2H); 3.0 (m, 2H); 2.9 (m, 2H).
MS [m+1]: 429

EXAMPLE 52

N-[3-(3-Methoxypropyl)-2,3,4,5-Tetrahydro-1H-3-Benzazepin-7-yl]-4-(Trifluoromethyl)Benzenesulfonamide Hydrochloride $^1$H-NMR (500 MHz, DMSO): 10.6 (s, 1H); 10.5 (bs, 1H); 8.0 (s, 4H); 7.1 (d, 1H); 7.0 (s, 1H); 6.9 (d, 1H); 3.6 (m, 2H); 3.3 (m, 4H); 3.2 (s, 3H); 3.1 (m, 2H); 2.9 (m, 4H); 2.0 (m, 2H).
MS [m+1]: 443

EXAMPLE 53

N-{3-[2-(4-(Fluorophenyl)Ethyl]-2,3,4,5-Tetrahydro-1H-3-Benzazepin-7-yl}-4-(Trifluoromethyl)Benzenesulfonamide Hydrochloride $^1$H-NMR (500 MHz, DMSO): 10.6 (m, 2H); 8.0 (s, 4H); 7.3 (dd?, 2H); 7.2 (dd?, 2H); 7.1 (d, 1H); 7.0 (s, 1H); 6.9 (d, 1H); 3.7 (m, 2H); 3.3 (m, 4H); 3.1 (m, 2H); 3.0 (m, 4H).
MS [m+1]: 493

EXAMPLE 54

N-[3-(3-Phenylpropyl)-2,3,4,5-Tetrahydro-1H-3-Benzazepin-7-yl]4-(Trifluoromethyl)Benzenesulfonamide Hydrochloride $^1$H-NMR (500 MHz, DMSO): 10.7 (bs, 1H); 10.6 (s, 1H); 8.0 (s, 4H); 7.3 (m, 2H); 7.2 (m, 3H); 7.1 (d, 1H); 7.0 (s, 1H); 6.9 (d, 1H); 3.7 (m, 2H); 3.3 (m, 2H); 3.1 (m, 2H); 2.9 (m, 4H); 2.7 (m, 2H); 2.0 (m, 2H).
MS [m+1]: 489

EXAMPLE 55

N-[3-(Cyclohexylmethyl)-2,3,4,5-Tetrahydro-1H-3-Benzazepin-7-yl]-4-Isopropylbenzenesulfonamide Hydrochloride MS [m+1]: 441

EXAMPLE 56

4-Isopropyl-N-(3-Methyl-2,3,4,5-Tetrahydro-1H-3-Benzazepin-7-yl)Benzenesulfonamide Hydrochloride MS [m+1]: 359

EXAMPLE 57

N-(3-Cyclopropylmethyl-2,3,4,5-Tetrahydro-1H-3-Benzazepin-7-yl)4-Isopropylbenzenesulfonamide Hydrochloride MS [m+1]: 399

EXAMPLE 58

N-(3-Allyl-2,3,4,5-Tetrahydro-1H-3-Benzazepin-7-yl)4-(Trifluoromethyl)Benzenesulfonamide Hydrochloride Method B 220 mg (0.54 mmol) of N-(2,3,4,5-tetrahydro-1H-3-benzazepin-7-yl)-4-(trifluoromethyl)-benzenesulfonamide and 70 µl (0.81 mmol) of allyl bromide were dissolved in 10 ml of dimethylformamide and, at room temperature, 0.30 ml (2.16 mmol) of triethylamine was added. After stirring at room temperature for 30 minutes, 50 ml of water were added, and the mixture was extracted twice with diethyl ether. The combined organic phases were dried with sodium sulfate and evaporated, and the residue was converted into the hydrochloride with ethereal hydrochloric acid. Yield: 160 mg (57% of theory)

$^1$H-NMR (500 MHz, DMSO): 10.9 (bs, 1H); 10.6 (s, 1H); 8.0 (s, 4H); 7.1 (d, 1H); 7.0 (s, 1H); 6.9 (d, 1H); 6.0 (m, 1H); 5.5 (m, 2H); 3.8 (m, 2H); 3.6 (m, 2H); 3.3 (m, 2H); 2.9 (m, 4H).
MS [m+1]: 411

The compounds of Examples 59 to 66 were prepared in a manner analogous to Example 58.

EXAMPLE 59

N-(3-Prop-2-ynyl-2,3,4,5-tetrahydro-1H-3-benzazepin-7-yl)4-(Trifluoromethyl)Benzenesulfonamide Hydrochloride $^1$H-NMR (500 MHz, DMSO): 11.4 (bs, 1H); 10.6 (s, 1H); 8.0 (s, 4H); 7.1 (d, 1H); 7.0 (s, 1H); 6.9 (d, 1H); 4.2 (m, 2H); 3.9 (bs, 1H), 3.7 (m, 2H); 3.3 (m, 2H); 2.9 (m, 4H).
MS [m+1]: 409

EXAMPLE 60

N-[3-(3-Fluoropropyl)-2,3,4,5-Tetrahydro-1H-3-Benzazepin-7-yl]-4-(Trifluoromethyl)Benzenesulfonamide Hydrochloride $^1$H-NMR (500 MHz, DMSO): 10.9 (bs, 1H); 10.6 (s, 1H); 8.0 (s, 4H); 7.1 (d, 1H); 7.0 (s, 1H); 6.9 (d, 1H); 4.6 (m, 1H); 4.5 (m, 1H); 3.7 (m, 2H); 3.3 (m, 2H); 3.2 (m, 2H); 2.9 (m, 4H); 2.2 (m, 2H).
MS [m+1]: 431

EXAMPLE 61

N-[3-(3-Phenoxypropyl)-2,3,4,5-Tetrahydro-1H-3-Benzazepin-7-yl]-4-(Trifluoromethyl)Benzenesulfonamide Hydrochloride The abovementioned compound was obtained by reacting N-(2,3,4,5-tetrahydro-1H-3-benzazepin-7-yl)4-(trifluoromethyl)benzenesulfonamide with (3-bromopropoxy)benzene.
$^1$H-NMR (500 MHz, DMSO): 10.7 (bs, 1H); 10.6 (s, 1H); 8.0 (s, 4H); 7.3 (t, 2H); 7.1 (d, 1H); 7.0 (s, 1H); 6.9 (m, 3H); 4.0 (m, 2H); 3.7 (m, 2H); 3.3 (m, 4H); 3.0 (m, 4H); 2.2 (m, 2H).
MS [m+1]: 505

EXAMPLE 62

N-[3-(2,2-Difluoroethyl)-2,3,4,5-Tetrahydro-1H-3-Benzazepin-7-yl]4-(Trifluoromethyl)Benzenesulfonamide Hydrochloride $^1$H-NMR (500 MHz, DMSO): 11.5 (bs, 1H); 10.6 (s, 1H); 8.0 (s, 4H); 7.1 (d, 1H); 7.0 (s, 1H); 6.9 (d, 1H); 6.7 (m, 1H); 3.7 (m, 4H); 3.3 (m, 2H); 3.1 (m, 2H); 3.0 (m, 2H).
MS [m+1]: 435

EXAMPLE 63

N-[3-(4-Fluorobutyl)-2,3,4,5-Tetrahydro-1H-3-Benzazepin-7-yl]-4-(Trifluoromethyl)Benzenesulfonamide Hydrochloride $^1$H-NMR (500 MHz, DMSO): 10.7 (bs, 1H); 10.6 (s, 1H); 8.0 (s, 4H); 7.3 (m, 2H); 7.2 (m, 3H); 7.1 (d, 1H); 7.0 (s, 1H); 6.9 (d, 1H); 4.5 (m, 1H); 4.4 (m, 1H); 3.6 (m, 2H); 3.3 (m, 2H); 3.1 (m, 2H); 2.9 (m, 4H); 1.8 (m, 2H); 1.7 (m, 2H).
MS [m+1]: 431

EXAMPLE 64

N-(3-Butyl-2,3,4,5-Tetrahydro-1H-3-Benzazepin-7-yl)4-(Trifluoromethyl)Benzenesulfonamide Hydrochloride $^1$H-NMR (500 MHz, DMSO): 10.7 (bs, 1H); 10.6 (s, 1H); 8.0 (s, 4H); 7.1 (d, 1H); 7.0 (s, 1H); 6.9 (d, 1H); 3.6 (m, 2H); 3.3 (m, 2H); 3.1 (m, 2H); 2.9 (m, 4H); 1.7 (m, 2H); 1.3 (m, 2H); 0.9 (t, 3H).
MS [m+1]: 427

EXAMPLE 65

N-(3-Allyl-2,3,4,5-Tetrahydro-1H-3-Benzazepin-7-yl)-4-(Isopropyl)Benzenesulfonamide Hydrochloride MS [m+1]: 385

EXAMPLE 66

N-[3-(3-Fluoropropyl)-2,3,4,5-Tetrahydro-1H-3-Benzazepin-7-yl]-4-Isopropylbenzenesulfonamide Hydrochloride MS [m+1]: 405

EXAMPLE 67

N-[3-(2-Fluoroethyl)-2,3,4,5-Tetrahydro-1H-3-Benzazepin-7-yl]-4-(Trifluoromethyl)Benzenesulfonamide Hydrochloride Method C 67.1 N-[3-(Fluoroacetyl)-2,3,4,5-tetrahydro-1H-3-benzazepin-7-yl]-4-(trifluoromethyl)benzenesulfonamide 700 mg (1.89 mmol) of N-(2,3,4,5-tetrahydro-1H-3-benzazepin-7-yl)4-(trifluoromethyl)benzenesulfonamide and 109 µl (1.89 mmol) of fluoroacetyl chloride were dissolved in 10 ml of tetrahydrofuran and, at room temperature, 0.79 ml (5.67 mmol) of triethylamine was added. After stirring at room temperature for 5 minutes, the solvent was evaporated off. The residue was taken up in 20 ml of water and extracted with 50 ml of diethyl ether. The organic phase was dried with sodium sulfate and then evaporated to dryness. Yield: 600 mg (65% of theory)

$^1$H-NMR (500 MHz, DMSO): 10.4 (bs, 1H); 8.0 (s, 4H); 7.0 (d, 1H); 6.9 (s, 1H); 6.8 (d, 1H); 5.2 (s, 1H); 5.1 (s, 1H); 3.5 (m, 2H); 3.3 (m, 2H); 2.8 (m, 2H); 2.7 (m, 2H).
MS [m+1]: 431

67.2 N-[3-(2-Fluoroethyl)-2,3,4,5-tetrahydro-1H-3-benzazepin-7-yl]-4-trifluoromethyl)benzenesulfonamide hydrochloride 3 ml of a 1.5 molar solution of borane in tetrahydrofuran (4.5 mmol) were introduced into 20 ml of tetrahydrofuran under a nitrogen atmosphere at room temperature. 300 mg (0.61 mmol) of N-[3-(fluoroacetyl)-2,3,4,5-tetrahydro-1H-3-benzazepin-7-yl]-4-(trifluoromethyl)benzenesulfonamide were dissolved in 10 ml of tetrahydrofuran. This solution was added dropwise to the reaction vessel, and the reaction mixture was heated to reflux for 6 hours. The solvent was then removed. The residue was mixed with 30 ml of water, acidified with dilute hydrochloric acid and extracted with 50 ml of diethyl ether. The aqueous phase was made alkaline with dilute sodium hydroxide solution and extracted with ethyl acetate. The combined organic phases were dried with sodium sulfate and evaporated, and the residue was converted into the hydrochloride with ethereal hydrochloric acid. Yield: 143 mg (47% of theory)

$^1$H-NMR (500 MHz, DMSO): 10.9 (bs, 1H); 10.6 (s, 1H); 8.0 (s, 4H); 7.1 (d, 1H); 7.0 (s, 1H); 6.9 (d, 1H); 4.9 (m, 1H); 4.8 (m, 1H); 3.7 (m 2H); 3.6 (m, 1H); 3.5 (m, 1H); 3.3 (m, 2H); 3.0 (m, 2H); 2.9 (m, 2H).
MS [m+1]: 417

B) Examples of Pharmaceutical Forms
Tablets:
Tablets of the following composition were compressed in a tablet press in a conventional way:

40 mg of substance of Examples 2
120 mg of corn starch
13.5 mg of gelatine
45 mg of lactose
2.25 mg of Aerosil® (chemically pure silica in submicroscopically fine dispersion)
6.75 mg of potato starch (as 6% paste)
Sugar-coated tablets:
20 mg of substance of Examples 2
60 mg of core composition
70 mg of sugar-coating composition
The core composition consists of 9 parts of corn starch, 3 parts of lactose and 1 part of vinylpyrrolidone/vinyl acetate 60:40 copolymer. The sugar-coating composition consists of 5 parts of sucrose, 2 parts of corn starch, 2 parts of calcium carbonate and 1 part of talc. The sugar-coated tablets produced in this way are subsequently provided with an enteric coating.

C) Biological Investigations—Receptor-Binding Studies:
The substance to be tested was dissolved either in methanol/Chremophor®) (BASF-AG) or in dimethyl sulfoxide and then diluted with water to the desired concentration.

I. Dopamine $D_3$ Receptor:
The mixture (0.250 ml) was composed of membranes from ~$10^6$ HEK-293 cells with stably expressed human dopamine $D_3$ receptors, 0.1 nM [$^{125}$I]-iodosulpride and incubation buffer (total binding) or additionally test substance (inhibition plot) or 1 µM spiperone (nonspecific binding). Triplicate assays were carried out.

The incubation buffer contained 50 mM Tris, 120 mM NaCl, 5 mM KCl, 2 mM $CaCl_2$, 2 mM $MgCl_2$ and 0.1% bovine serum albumin, 10 µM quinolone, 0.1% ascorbic acid (prepared freshly each day). The buffer was adjusted to pH 7.4 with HCl.

II. Dopamine $D_{2L}$ receptor:
The mixture (1 ml) was composed of membranes from ~$10^6$ HEK-293 cells with stably expressed human dopamine $D_{2L}$ receptors (long isoform) and 0.01 nM [$^{125}$I]-iodospiperone and incubation buffer (total binding) or additionally test substance (inhibition plot) or 1 µM haloperidol (nonspecific binding). Triplicate assays were carried out.

The incubation buffer contained 50 mM Tris, 120 mM NaCl, 5 mM KCl, 2 mM $CaCl_2$, 2 mM $MgCl_2$ and 0.1% bovine serum albumin. The buffer was adjusted to 7.4 with HCl.

III. Measurement and Evaluation:
After incubation at 25° C. for 60 minutes, the mixtures were filtered through Wathman GF/B glass fiber filters under vacuum using a cell harvester. The filters were transferred using a filter transfer system into scintillation vials. After addition of 4 ml of Ultima Gold® (Packard), the samples were shaken for one hour and then the radioactivity was counted in a Beta Counter (Packard, Tricarb 2000 or 2200CA). The cp values were converted into dpm on the basis of a standard quench series with the aid of the program supplied with the instrument.

The inhibition plots were evaluated by iterative nonlinear regression analysis using the Statistical Analysis System (SAS), similar to the "LIGAND" program described by Munson and Rodbard.

The compounds of the invention show very good affinities for the $D_3$ receptor in these assays (<100 nM, frequently <50 nM) and bind selectively to the $D_3$ receptor. The results of the binding assays are indicated in Table 1.

TABLE 1

| Example | $K_i$ ($D_3$) [nM] | Selectivity vs. $D_2L$* |
|---|---|---|
| 2 | 7.1 | 99 |
| 3 | 4.1 | 68 |
| 4 | 0.5 | 435 |
| 5 | 1 | 368 |
| 6 | 5.8 | 252 |
| 7 | 4.1 | 120 |
| 8 | 0.3 | 330 |
| 10 | 16.5 | 271 |
| 11 | 4.7 | 112 |
| 12 | 7.2 | 90 |
| 13 | 0.6 | 143 |
| 14 | 3.6 | 113 |
| 16 | 8.1 | 142 |
| 17 | 4.5 | 68 |
| 18 | 7.3 | 85 |
| 19 | 3 | 65 |
| 20 | 7.1 | 85 |
| 21 | 16 | 47 |
| 22 | 13 | 46 |
| 31 | 1 | 63 |
| 35 | 28.2 | 40 |
| 36 | 1 | 446 |
| 56 | 1.2 | 66 |
| 57 | 2.1 | 115 |
| 58 | 3.4 | 84 |
| 65 | 0.4 | 141 |
| 66 | 1.2 | 146 |

*$K_i(D_{2L})/K_i(D_3)$

We claim:
1. A tetrahydrobenzazepine of the formula I

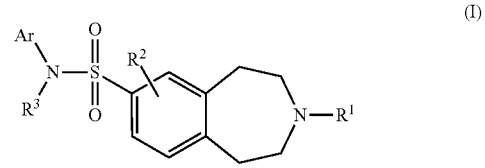

(I)

in which
Ar is an aromatic radical which is selected from phenyl and a 5- or 6-membered heteroaromatic radical having 1, 2, 3 or 4 heteroatoms which are selected independently of one another from O, N and S, where the aromatic radical may have 1, 2 or 3 substituents which are selected independently of one another from $C_1$-$C_6$-alkyl which is optionally substituted one or more times by OH, $C_1$-$C_4$-alkoxy, halogen or phenyl, or $C_2$-$C_6$-alkenyl which is optionally substituted one or more times by OH, $C_1$-$C_4$-alkoxy, halogen or phenyl, or $C_2$-$C_6$-alkynyl which is optionally substituted one or more times by OH, $C_1$-$C_4$-alkoxy, halogen or phenyl, or $C_3$-$C_6$-cycloalkyl which is optionally substituted one or more times by OH, $C_1$-$C_4$-alkoxy, halogen, phenyl or $C_1$-$C_4$-alkyl, or halogen, CN, $OR^4$, $COOR^4$, $NR^5R^6$, $CONR^5R^6$, $NO_2$, $SR^7$, $SO_2R^7$, $SO_2NR^5R^6$, $COR^8$, and phenyl which optionally has one, two or three substituents which are selected independently of one another from $C_1$-$C_4$-alkyl, $C_1$-$C_4$-alkoxy, $NR^5R^6$, CN, $C_1$-$C_2$-fluoroalkyl or halogen, where phenyl and the heterocyclic radical may also be fused to a 5- or 6-membered aromatic or nonaromatic carbocycle, or phenyl may be fused to a 5- or 6-membered aromatic or nonaromatic heterocycle which has 1, 2 or 3 heteroatoms selected from O, N and S;

R¹ is hydrogen, $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_1$-$C_8$-alkylcarbonyl, $C_1$-$C_8$-haloalkylcarbonyl or substituted $C_1$-$C_8$-alkyl which carries a substituent which is selected from OH, $C_1$-$C_4$-alkoxy, $C_1$-$C_4$-alkylamino, di-($C_1$-$C_4$-alkyl)amino, phenyl, phenoxy, $C_3$-$C_8$-cycloalkyl and $C_3$-$C_8$-cycloalkyloxy, where the last four groups mentioned may optionally have one or more substituents selected from OH, CN, $NO_2$, $C_1$-$C_4$-alkyl, $C_1$-$C_4$-haloalkyl, $C_1$-$C_4$-alkoxy, $C_1$-$C_4$-haloalkoxy and halogen;

R² is hydrogen, halogen, $C_1$-$C_4$-alkyl, $C_1$-$C_4$-alkoxy, $C_1$-$C_4$-haloalkyl, $C_1$-$C_4$-haloalkoxy, OH, $NO_2$, CN, $COOR^4$, $NR^5R^6$ or $CONR^5R^6$;

R³ is hydrogen, $C_1$-$C_4$-alkyl, $C_1$-$C_4$-alkoxy, $C_1$-$C_4$-alkylcarbonyl, phenyl, phenyl-$C_1$-$C_4$-alkyl or phenylcarbonyl, where phenyl in the last three radicals mentioned may optionally have 1, 2 or 3 substituents which are selected independently of one another from $C_1$-$C_4$-alkyl, $C_1$-$C_4$-haloalkyl, $C_1$-$C_4$-alkoxy and halogen;

$R^4$, $R^5$, $R^6$, $R^7$, and $R^8$ are independently of one another H, $C_1$-$C_6$-alkyl which may carry a substituent selected from OH, $C_1$-$C_4$-alkoxy and optionally substituted phenyl, $C_1$-$C_6$-haloalkyl or phenyl, where $R^6$ may also be a group $COR^9$ in which $R^9$ is H, $C_1$-$C_6$-alkyl which is optionally substituted by OH, $C_1$-$C_4$-alkoxy or optionally substituted phenyl, or $C_1$-$C_6$-haloalkyl or phenyl, where $R^5$ with $R^6$ may also together with the nitrogen atom to which they are bonded be a 5- or 6-membered saturated or unsaturated N-heterocycle which may optionally have a further heteroatom selected from O, S and $NR^{10}$ as ring member, where $R^{10}$ hydrogen or $C_1$-$C_4$-alkyl;

the N-oxides of this compound, the physiologically tolerated acid addition salts of this compound and the physiologically tolerated acid addition salts of the N-oxides of formula I.

2. A tetrahydrobenzazepine of the formula I as claimed in claim 1, in which R² is hydrogen.

3. A tetrahydrobenzazepine of formula I as claimed in claim 1, in which Ar is phenyl which may be substituted as claimed in claim 1.

4. A tetrahydrobenzazepine of the formula I as claimed in claim 3, in which phenyl is unsubstituted or has 1 or 2 substituents, of which one substituent is arranged in the para postion relative to the variable $NR^3$.

5. A tetrahydrobenzazepine of the formula I as claimed in claim 3, in which the substituents on the phenyl are selected from $C_2$-$C_6$-alkyl, $C_2$-$C_6$-alkenyl, $C_2$-$C_6$-alkynyl and $C_1$-$C_2$-fluoroalkyl.

6. A compound as claimed in claim 1, wherein Ar is phenyl which carries a radical $R^P$ which is located in the para position of the phenyl ring wherein $R^P$ has the following formula $R^{P'}$:

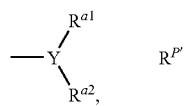

wherein
Y is N, CH or CF,
$R^{a1}$ and $R^{a2}$ are independently of each other selected from $C_1$-$C_2$-alkyl, fluorinated $C_1$-$C_2$-alkyl, provided for Y being CH or CF one of the radicals $R^{a}1$ or $R^{a2}$ may also be hydrogen or fluorine, or $R^{a1}$ and $R^{a2}$ form a radical $(CH_2)_m$ wherein 1 or 2 of the hydrogen atoms may be replaced by fluorine and wherein m is 2, 3 or 4.

7. A tetrahydrobenzazepine of the formula I as claimed in claim 1, in which Ar is a 5- or 6-membered heteroaromatic radical having 1, 2, 3 or 4 heteroatoms which are selected independently of one another from O, N and S, where the heteroaromatic radical may be substituted as claimed in claim 1.

8. A tetrahydrobenzazepine of the formula I as claimed in claim 1, in which R¹ has the formula $CH_2$—$R^{1a}$ in which $R^{1a}$ is $C_1$-$C_7$-alkyl, $C_1$-$C_7$-haloalkyl, $C_2$-$C_7$-alkenyl, $C_2$-$C_7$-haloalkenyl, $C_2$-$C_7$-alkynyl, $C_2$-$C_7$-haloalkynyl or $C_1$-$C_7$-alkyl which has a substituent which is selected from OH, $C_1$-$C_4$-alkoxy, $C_1$-$C_4$-alkylamino, di-($C_1$-$C_4$-alkyl)amino, phenyl, phenoxy, $C_3$-$C_8$-cycloalkyl and $C_3$-$C_8$-cycloalkyloxy, where the last four groups mentioned may optionally have one or more substituents selected from $C_1$-$C_4$-alkyl, $C_1$-$C_4$-haloalkyl, $C_1$-$C_4$-alkoxy and halogen.

9. A tetrahydrobenzazepine of the formula I as claimed in claim 8, in which $R^{1a}$ is $C_1$-$C_7$-alkyl, $C_2$-$C_7$-alkenyl, $C_2$-$C_7$-alkynyl, $C_3$-$C_8$-cycloalkyl or $C_1$-$C_7$-fluoroalkyl.

10. A tetrahydrobenzazepine as claimed in claim 1, wherein $R^P$ is selected from a radical of the formula

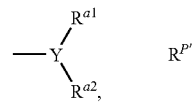

wherein
Y is N, CH or CF,
$R^{a1}$ and $R^{a2}$ are independently of each other selected from $C_1$-$C_2$-alkyl, fluorinated $C_1$-$C_2$-alkyl, provided for Y being CH or CF one of the radicals $R^{a1}$ or $R^{a2}$ may also be hydrogen or fluorine, or $R^{a1}$ and $R^{a2}$ form a radical $(CH_2)_m$ wherein 1 or 2 of the hydrogen atoms may be replaced by fluorine and wherein m is 2, 3 or 4;
and $R^{1a}$ is ethyl.

11. A tetrahydrobenzazepine as claimed in claim 10, wherein $R^P$ is selected from isopropyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, 1-fluoro-1-methylethyl, cyclopropyl, cyclobutyl, 1-fluorocyclopropyl, 2,2-difluorocyclopropyl and 2-fluorocyclopropyl.

12. A pharmaceutical composition comprising at least one active ingredient selected from compound of the formula I as claimed in claim 1, the physiologically tolerated acid addition salts of formula I, the N-oxides of compounds of the formula I, and the physiologically tolerated acid addition salts of the N-oxides of formula I, where appropriate together with physiologically acceptable carriers and/or excipients.

13. A method for treating a medical disorder susceptible to treatment with a dopamine D3 receptor ligand, said method comprising administering an effective amount of at least one compound as claimed in claim 1 to a subject in need thereof, wherein the medical disorder is selected from the group consisting of schizophrenia, depression, parkinsonism, and renal function disorders.

14. The method as claimed in claim 13, wherein the medical disorder is selected from the group consisting of schizophrenia, depression and parkinsonism.

15. The method as claimed in claim 13, wherein the medical disorder is a renal function disorders.

* * * * *

UNITED STATES PATENT AND TRADEMARK OFFICE
CERTIFICATE OF CORRECTION

PATENT NO. : 8,207,160 B2
APPLICATION NO. : 10/583590
DATED : June 26, 2012
INVENTOR(S) : Wilfried Braje et al.

Page 1 of 1

It is certified that error appears in the above-identified patent and that said Letters Patent is hereby corrected as shown below:

Title Page

Item 60 in the Related U.S. Application Data section, please add the following:

-- Application No. 10/740,092, filed on December 18, 2003, now abandoned. --

Signed and Sealed this
Twenty-eighth Day of May, 2013

Teresa Stanek Rea
*Acting Director of the United States Patent and Trademark Office*